US012606550B2

(12) United States Patent
Schwaebe et al.

(10) Patent No.: US 12,606,550 B2
(45) Date of Patent: Apr. 21, 2026

(54) METHODS FOR SYNTHESIS OF CHK1 INHIBITORS

(71) Applicant: CRT PIONEER FUND LP, Berkhamsted (GB)

(72) Inventors: Michael Schwaebe, San Mateo, CA (US); Thorsten Rosner, San Mateo, CA (US); Dalian Zhao, San Mateo, CA (US); Ross Miller, San Mateo, CA (US); Rich Dulina, San Mateo, CA (US); Michael Humora, San Mateo, CA (US); Stephen E. Gottschling, San Mateo, CA (US)

(73) Assignee: CRT Pioneer Fund LP (GB)

(*) Notice: Subject to any disclaimer, the term of this patent is extended or adjusted under 35 U.S.C. 154(b) by 721 days.

(21) Appl. No.: 17/995,564

(22) PCT Filed: Apr. 6, 2021

(86) PCT No.: PCT/US2021/025977
§ 371 (c)(1),
(2) Date: Oct. 5, 2022

(87) PCT Pub. No.: WO2021/207210
PCT Pub. Date: Oct. 14, 2021

(65) Prior Publication Data

US 2023/0150994 A1 May 18, 2023

Related U.S. Application Data

(60) Provisional application No. 63/006,305, filed on Apr. 7, 2020.

(51) Int. Cl.
*C07D 413/14* (2006.01)

(52) U.S. Cl.
CPC ........ *C07D 413/14* (2013.01); *C07B 2200/13* (2013.01)

(58) Field of Classification Search
None
See application file for complete search history.

(56) References Cited

U.S. PATENT DOCUMENTS 3,773,778 A 11/1973 Hoehn et al.
4,107,288 A 8/1978 Oppenheim et al.
(Continued)

FOREIGN PATENT DOCUMENTS

CA 2870837 A1 11/2013
CN 1594392 A 3/2005
(Continued)

OTHER PUBLICATIONS

Atipamula et al., Cryst. Growth Des. 2012, 12, 5, 2147-2152 (Year: 2012).*
(Continued)

*Primary Examiner* — Jeffrey S Lundgren
*Assistant Examiner* — Anthony Joseph Seitz
(74) *Attorney, Agent, or Firm* — Foley Hoag LLP; David P. Halstead; Alexander J. Chatterley

(57) ABSTRACT

The present technology relates to processes, compounds, compositions, and methods useful for coupling reactions. Also, the present disclosure provides for novel intermediates, compositions of matter, and processes relating to the Chk1 inhibitor, SRA737.

3 Claims, 8 Drawing Sheets

(56) References Cited

U.S. PATENT DOCUMENTS

| | | | |
|---|---|---|---|
| 5,145,684 | A | 9/1992 | Liversidge et al. |
| 8,058,045 | B2 | 11/2011 | Collins et al. |
| 8,367,658 | B2 | 2/2013 | Collins et al. |
| 8,530,468 | B2 | 9/2013 | Collins et al. |
| 8,618,121 | B2 | 12/2013 | Collins et al. |
| 9,040,540 | B2 | 5/2015 | Collins et al. |
| 9,155,726 | B2 | 10/2015 | Humphries et al. |
| 9,345,705 | B2 | 5/2016 | Shumway et al. |
| 9,403,797 | B2 | 8/2016 | Collins et al. |
| 9,663,503 | B2 | 5/2017 | Collins et al. |
| 9,765,059 | B2 | 9/2017 | Collins et al. |
| 10,259,806 | B2 | 4/2019 | Collins et al. |
| 11,596,637 | B2 | 3/2023 | Hassig et al. |
| 11,787,792 | B2 | 10/2023 | Collins et al. |
| 2005/0215556 | A1 | 9/2005 | Lin et al. |
| 2010/0210639 | A1 | 8/2010 | Collins et al. |
| 2010/0249112 | A1 | 9/2010 | O'Connor et al. |
| 2010/0311730 | A1 | 12/2010 | Collins et al. |
| 2010/0331328 | A1 | 12/2010 | Collins et al. |
| 2011/0054001 | A1 | 3/2011 | Look et al. |
| 2012/0040967 | A1 | 2/2012 | Collins et al. |
| 2014/0045782 | A1 | 2/2014 | Humphries et al. |
| 2014/0141024 | A1 | 5/2014 | Jure-Kunkel et al. |
| 2014/0315925 | A1 | 10/2014 | Collins et al. |
| 2014/0343071 | A1 | 11/2014 | Shumway et al. |
| 2015/0005263 | A1 | 1/2015 | Hart et al. |
| 2015/0126471 | A1 | 5/2015 | Collins et al. |
| 2015/0225372 | A1 | 8/2015 | Collins et al. |
| 2016/0208339 | A1 | 7/2016 | So et al. |
| 2016/0289686 | A1 | 10/2016 | Kemp et al. |
| 2017/0087185 | A1 | 3/2017 | Crane et al. |
| 2017/0158776 | A1 | 6/2017 | Feltquate et al. |
| 2018/0022739 | A1 * | 1/2018 | Collins ................ C07D 413/14 435/375 |
| 2019/0085403 | A1 | 3/2019 | Frampton et al. |
| 2020/0157638 | A1 | 5/2020 | Hassig et al. |
| 2020/0397796 | A1 | 12/2020 | Hassig et al. |
| 2022/0184091 | A1 | 6/2022 | Hassig et al. |
| 2022/0226338 | A1 | 7/2022 | Hassig et al. |

FOREIGN PATENT DOCUMENTS

| | | | |
|---|---|---|---|
| CN | 102675858 | A | 9/2012 |
| CN | 103476770 | A | 12/2013 |
| CN | 104302635 | A | 1/2015 |
| CN | 112469391 | A | 3/2021 |
| EA | 200800441 | A1 | 8/2008 |
| EP | 3210980 | | 8/2017 |
| JP | 2010540610 | A | 12/2010 |
| JP | 2015-520753 | A | 7/2015 |
| KR | 102341637 | B1 | 12/2021 |
| RU | 2009110255 | A | 9/2010 |
| WO | WO-1995/019970 | A1 | 7/1995 |
| WO | WO-1997/002266 | A1 | 1/1997 |
| WO | WO-01/51919 | A2 | 7/2001 |
| WO | WO-2003/032984 | A1 | 4/2003 |
| WO | WO-2003/035065 | A1 | 5/2003 |
| WO | WO-2003/037898 | | 5/2003 |
| WO | WO-2003/093297 | A2 | 11/2003 |
| WO | WO-2003/101444 | A1 | 12/2003 |
| WO | WO-2005/011597 | A2 | 2/2005 |
| WO | WO-2005/034869 | A2 | 4/2005 |
| WO | WO-2005/037285 | A1 | 4/2005 |
| WO | WO-2005/037825 | A2 | 4/2005 |
| WO | WO-2005/047294 | A1 | 5/2005 |
| WO | WO-2005/121126 | A1 | 12/2005 |
| WO | WO-2006/039718 | A2 | 4/2006 |
| WO | WO-2006/116733 | A2 | 11/2006 |
| WO | WO-2007/000240 | A1 | 1/2007 |
| WO | WO-2007/041712 | A1 | 4/2007 |
| WO | WO-2007/044779 | A1 | 4/2007 |
| WO | WO-2007/089191 | A1 | 8/2007 |
| WO | WO-2008/077554 | A1 | 7/2008 |
| WO | WO-2008/115369 | A2 | 9/2008 |
| WO | WO-2008/117050 | A1 | 10/2008 |
| WO | WO-2009/004329 | A1 | 1/2009 |
| WO | WO-2009/044162 | A1 | 4/2009 |
| WO | WO-2009/103966 | A1 | 8/2009 |
| WO | WO-2011029027 | A1 | 3/2011 |
| WO | WO-2013/068755 | A1 | 5/2013 |
| WO | WO-2013/096687 | A1 | 6/2013 |
| WO | WO-2013/103836 | A2 | 7/2013 |
| WO | WO-2013/171470 | A1 | 11/2013 |
| WO | WO-2018/102613 | A2 | 6/2018 |
| WO | WO-2018/191277 | A1 | 10/2018 |
| WO | WO-2018/191299 | A1 | 10/2018 |
| WO | WO-2018/222970 | A1 | 12/2018 |
| WO | WO-2019/012030 | A1 | 1/2019 |
| WO | WO-2019/165458 | A1 | 8/2019 |
| WO | WO-2020/198510 | A1 | 10/2020 |
| WO | WO-2020/232154 | A2 | 11/2020 |
| WO | WO-2021207210 | A1 | 10/2021 |

OTHER PUBLICATIONS

Altschul et al., "Basic Local Alignment Search Tool," J. Mol. Biol., Oct. 1990, 215:403-410.

Anderson et al., "Preparation of water-soluble organic compounds by salt formation" Technobiology, vol. 1999, No. 09.

Anonymous, "Establishment of Standards and Test Methods for New Pharmaceuticals." Pharmaceutical Trial No. 568, Jan. 1, 2001.

Booth et al., "The CHK1 inhibitor SRA737 synergizes with PARP1 inhibitors to kill carcinoma cells", Cancer Biology & Therapy, 2018, vol. 19, No. 9, 786-796.

Brandsma, Inger et al. Directing the Use of Ddr Kinase Inhibitors in Cancer Treatment. Expert Opinion on Investigational Drugs vol. 26,12: pp. 1341-1355 (2017).

Bryant et al. Inhibition of the checkpoint kinase Chkl induces DNA damage and cell death in human Leukemia and Lymphoma cells. Mol Cancer. 13:147 (2014).

Carey, F A et al. Advanced Organic Chemistry, 3rd Edition. vols. A and B, Plenum Press (1992).

Chalmers et al., "Analysis of 100,000 human cancer genomes reveals the landscape of tumor mutational burden," Genome Medicine, 2017, 9(34): 1-14.

Cheson et al., "Revised Response Criteria for Malignant Lymphoma," Journal of Clinical Oncology, Feb. 2007, 25(5):579-586.

ClinicalTrials.gov identifier: NCT02797964. Dye, A. A Phase ½ Trial of SRA737 in Subjects With Advanced Cancer. Retrieved from Internet on Aug. 16, 2023 URL: https://clinicaltrials.govict2/show/NCT02797964?term=SRA737draw=28rank=1 :16 Pages (2022).

ClinicalTrials.gov identifier: NCT02797977 :pp. 1-6 (2020). Sierra Oncology LLC - a GSK company. A Phase ½ Trial SRA737 in Combination With Gemcitabine and Cisplatin or Gemcitabine Alone in Advanced Cancer Subjects. Retrieved from the Internet URL: https://clinicaltrials.govict2/show/NCT02797977?term=SRA737&draw=28rank=2. Retrieved from Internet on Aug. 16, 2023.

ClinicalTrials.gov Identifier: NCT02854436. An Efficacy and Safety Study of Niraparib in Men With Metastatic Castration-Resistant Prostate Cancer and DNA-Repair Anomalies (Galahad). Record created Aug. 1, 2016. pp. 1-12. Retrieved May 21, 2024 at URL: https://clinicaltrials.gov/study/NCT02854436.

Colowick, Sidney P et al. Methods of Enzymology. Academic Press, Inc : pp. 1-418 (1990).

Creighton, Thomas E et al. Proteins: Structures and Molecular Properties, 2nd Edition, W.H. Freeman and Company (1993).

Eisenhauer et al., "New response evaluation criteria in solid tumours: revised RECIST guideline (version 1.1)," Eur. J. Cancer., Jan. 2009, 45(2):228-47.

Eltabbakh, Gamal H et al. Efficacy of a Modified Regimen of Gemcitabine and Cisplatin Among Women With Recurrent Epithelial Ovarian Cancer. Journal of Solid Tumors vol. 6,2: pp. 1-7 (2016).

Examination Report for EP Application No. 20806456.8 dated Nov. 14, 2024.

Faustino-Rocha et al., "Estimation of rat mammary tumor volume using caliper and ultrasonography measurements," Lab Anim (Ny), Jun. 2013, 42(6):217-24.

(56) References Cited

OTHER PUBLICATIONS

Final Office Action for U.S. Appl. No. 16/618,028 dated Oct. 10, 2023.
Final Office Action for U.S. Appl. No. 16/975,686 dated Mar. 14, 2024.
Final Office Action for U.S. Appl. No. 16/975,686 dated Oct. 17, 2022.
FoundationOne CDx, "Next generation sequencing oncology panel, somatic or 10. germline variant detection system," FDA Summary of Safety and Effectiveness Data (SSED), Nov. 30, 2017, 58 pages.
Grabocka et al., "Wild-type H-and N-Ras promote mutant K-Ras-driven tumorigenesis by modulating the DNA damage response." Cancer Cell 25(2) (2014): 243-256.
Guidance for Industry. Estimating the Maximum Safe Starting Dose in Initial Clinical Trials for Therapeutics in Adult Healthy Volunteers, U.S. Department of Health and Human Services-FDA: pp. 1-30 (2005). Retrieved from the Internet URL: https://www.fda.gov/media/72309/download.
Hansen, Ryan J et al. Abstract B181: The Chk1 inhibitor, SRA737, Demonstrates Chemical Synthetic Lethality With Replication Stress-inducing Agents, Including Low-dose Gemcitabine, in Preclinical Models of Cancer. Molecular Cancer Therapeutics: pp. 1-4 (2018).
Hirayama, "Handbook for Organic Compound Crystal Fabrication" 2008, 28 pages.
Hong et al., "Evaluation of prexasertib, a checkpoint kinase 1 inhibitor, in a phase Ib study of patients with squamous cell carcinoma." Clinical Cancer Research 24(14) (2018): 3263-3272.
Intemational Search Report and Written Opinion for International Application No. PCT/US20/25018 dated Jun. 19, 2020.
International Preliminary Report on Patentability for International Application No. PCT/US20/32722 dated Oct. 30, 2020.
International Search Report and Written Opinion for International Application No. PCT/US18/26917 dated Jul. 2, 2018.
International Search Report and Written Opinion for International Application No. PCT/US18/35566 dated Oct. 11, 2018.
International Search Report and Written Opinion for International Application No. PCT/US19/19643 dated Apr. 30, 2019.
International Search Report and Written Opinion for International Application No. PCT/US20/23722 dated Oct. 20, 2020.
Jensen et al., "Tumor volume in subcutaneous mouse xenografts measured by microCT is more accurate and reproducible than determined by 18F-FDG-microPET or external caliper," BMC Medical Imaging, Oct. 2008, 8:16.
Kawaguchi et al., "Medicinal and Crystalline polymorphism." Journal of Human Environmental Engineering, 2002, 4(2), p. 310-317.
Konstantinopoulos et al., "Homologous recombination deficiency: exploiting the fundamental vulnerability of ovarian cancer." Cancer Discovery 5(11) (2015): 1137-1154.
Lee, Jung-Min et al. Prexasertib, a cell cycle checkpoint kinase 1 and 2 inhibitor, in BRCA wild-type Recurrent High-grade Serous Ovarian Cancer: a First-in-class Proof-of-concept Phase 2 Study. Lancet Oncology vol. 19,2: pp. 207-215 (2018).
Lehninger, Albert L. Principles of Biochemistry 8th Edition. Worth Publishers, Inc (2021).
Li et al., "Design, synthesis and evaluation of novel non-ATP competitive CHK1 inhibitors as chemotherapy sensitizing agents", Journal of Chinese Pharmaceutical Sciences, 2016, 25(10), 726-736.
Lin, Aimee Bence et al. Achieving Precision Death with Cell-Cycle Inhibitors that Target DNA Replication and Repair. Clinical Cancer Research vol. 23,12: pp. 3232-3240 (2017).
Mitchell et al., "Poly (ADP-ribose) polymerase 1 modulates the lethality of CHK1 inhibitors in carcinoma cells." Molecular Pharmacology 78 (2010): 909-917.
Monga et al., "Intratumoral therapy of cisplatin/epinephrine injectable gel for palliation in patients with obstructive esophageal cancer," Am. J. Clin. Oncol., Aug. 2000, 23(4):386-392.
Needleman et al., "A general method applicable to the search for similarities in the amino acid sequence of two proteins," J. Mol. Biol.. Mar. 1970, 48:443-53.
Non-Final Office Action for U.S. Appl. No. 16/618,028 dated Jun. 11, 2024.
Non-Final Office Action for U.S. Appl. No. 16/618,028 dated Jun. 16, 2022.
Non-Final Office Action for U.S. Appl. No. 16/975,686 dated Feb. 11, 2022.
Non-Final Office Action for U.S. Appl. No. 16/975,686 dated Jul. 26, 2023.
Non-Final Office Action for U.S. Appl. No. 16/975,686 dated Oct. 29, 2021.
Notice of Allowance for U.S. Appl. No. 16/975,686 dated Aug. 2, 2024.
Office Action for JP Application No. 2022-561181 dated Feb. 19, 2025.
Ono, "Analysis of the Current State of Salt Selection." Journal of Pharmaceutical Sciences, 2013, 73(3),p. 176-182.
Oshima, "Crystallization of Polymorphs and Pseudo-polymorphs and Its Control." Pharm Stage,2007 , 6(10).
Partial European Search Report for EP Application No. 20806456.8 dated Feb. 10, 2023.
Pearson et al., "Improved tools for biological sequence comparison," Proc. Nat'l. Acad. Sci.,85(8):2444-2448 (1988).
prnewswire.com [ online], "Sierra Reports Late-Breaking Preclinical Data for SRA737 Presented at AACR 2019," Apr. 1, 2019, retrieved on Nov. 16, 2022, retrieved from URL<https://www.prnewswire.com/news-releases/sierra-rep011s-1ate-breaking-preclinical-data-for-sra737-presented-at-aacr-2019-300822099.html >, 4 pages.
Richtig et al., "Calculated tumour vol. as a prognostic parameter for survival in choroidal melanomas," Eye, 2004, 18:619-623.
Rundle et al., "Targeting the ATR-CHK1 axis in cancer therapy." Cancers 9 (2017): 41.
Sambrook, Joseph et al. Molecular Cloning: A Laboratory Manual, 2nd Edition. Cold Spring Harbor Laboratory Press : pp. 1-30 (1989).
Sandhu, Shahneen K, et al., The Poly(ADP-ribose) Polymerase Inhibitor Niraparib (MK4827) In BRCA Mutation Carriers And Patients With Sporadic Cancer: A Phase 1 Dose-escalation Trial. The Lancet Oncology 14(9):882-892 (2013).
Scher, Howard I, et al., Trial Design and Objectives for Castration-Resistant Prostate Cancer: Updated Recommendations From the Prostate Cancer Clinical Trials Working Group 3. Journal of Clinical Oncology 34(12):1402-1418 (2016).
Sen et al., "Combination treatment of the oral CHK1 inhibitor, SRA737, and low-dose gemcitabine enhances the effect of programmed death ligand 1 blockade by modulating the immune microenvironment in SCLC." Journal of Thoracic Oncology 14(12) (2019): 2152-2163.
Sen et al., "The oral CHK1 inhibitor, SRA737, synergizes with Immune Checkpoint blockade in small cell lung cancer ;SCLC)", MD Anderson Cancer Center, Nov. 21, 2018, p. 1.
Sen, Triparna et al. CHK1 Inhibition in Small-Cell Lung Cancer Produces Single-Agent Activity in Biomarker-Defined Disease Subsets and Combination Activity with Cisplatin or Olaparib. Cancer Research vol. 77,14: pp. 3870-3884 (2017).
Smith et al., "Comparison of biosequences," Adv. Appl. Math., Dec. 1981, 2(4):482-489.
Stahl, P Heinrich et al. Handbook of Pharmaceutical Salts: Properties, Selection, and Use. Verlag Helvetica Chimica Acta and Wiley-VCH (2002).
Supplementary European Search Report for EP Application No. 20776848.2 dated Nov. 25, 2022.
Supplementary European Search Report for EP Application No. 18784295.0 dated Dec. 9, 2020.
Supplementary European Search Report for EP Application No. 18809063.3 dated May 10, 2021.
Supplementary European Search Report for EP Application No. 19757456.9 dated Dec. 9, 2021.
Supplementary European Search Report for EP Application No. 20806456.8 dated May 11, 2023.
Takada, "API Form Screening and Selection in the Drug Discovery Phase." Pharm Stage, 6(10), 2007 p. 20-25.
Tomayko et al., "Determination of subcutaneous tumor size in athymic (nude) mice," Cancer Chemotherapy and Pharmacology, 1889, 24(3): 148-154.

(56) References Cited

OTHER PUBLICATIONS

Tong et al., "drexplorer: A tool to explore dose-response relationships and drug-drug interactionsm," Bioinformatics, May 15, 2015, 31(10): 1692-4.
Walton et al., "The clinical development candidate CCT245737 is an orally active CHK1 inhibitor with preclinical activity in RAS mutant NSCLC and E~t-MYC driven B-cell lymphoma," Oncotarget. Jan. 19, 2016, 7(3):2329-2342.
Wang et al., "Knockdown of Chkl, Weel and Mytl by RNA Interference Abrogates G2 Checkpoint and Induces Apoptosis," Cancer Biology & Therapy, Mar. 2004, 3(3):305-313.
Wang, Minhua et al. Screening for Microsatellite Instability in Colorectal Cancer and Lynch Syndrome—A Mini Review. North America Journal of Medicine and Science vol. 9,1: pp. 5-11 (2016).
Yamano, "Approach to crystal polymorphism phenomena in pharmaceutical process research." Journal of the Society of Synthetic Organic Chemistry, Jan. 1, 2007, 65(9).
Yin et al., "Chkl inhibition potentiates the therapeutic efficacy of PARP inhibitor BMN673 in gastric cancer." American Journal of Cancer Research 7(3) (2017): 473.
Yuan et al., "Research progress of Chk1 and its inhibitor", Modern Oncology, 2018, 26 (17):2797-2800.
Berge, Stephen M. et al. Pharmaceutical Salts. Journal of Pharmaceutical Sciences 66(1):1-19 (1977).
Co-pending U.S. Appl. No. 16/844,403, inventors IAN; Collins et al., filed on Apr. 9, 2020.
EP21784225.1 Extended European Search Report dated Jun. 4, 2024.
Gennaro et al. Remington's Pharmaceutical Sciences (18th ed., Mack Publishing Company. see especially Part 8 : Pharmaceutical preparations and their Manufacture (1990).
Osborne, James D et al. Multiparameter Lead Optimization to Give an Oral Checkpoint Kinase 1 (CHK1) Inhibitor Clinical Candidate: (R)-5-((4-((Morpholin-2-ylmethyl)amino)-5-(trifluoromethyl)pyridin-2-yl)amino)pyrazine-2-carbonitrile (CCT245737). Journal of Medicinal Chemistry vol. 59,11: pp. 5221-5237 (2016).
Rowe, et al., Handbook of Pharmaceutical Excipients : 5th Edition. The Pharmaceutical Press and the American Pharmaceutical Association. 884-918 (2005).
U.S. Appl. No. 14/396,338 Notice of Allowance dated Jan. 19, 2017.
U.S. Appl. No. 14/396,338 Office Action dated Aug. 24, 2016.
U.S. Appl. No. 15/587,270 Notice of Allowance dated Mar. 20, 2019.
U.S. Appl. No. 15/587,270 Notice of Allowance dated Nov. 20, 2018.
U.S. Appl. No. 15/587,270 Office Action dated Jun. 12, 2018.
U.S. Appl. No. 17/124,606 Notice of Allowance dated Jun. 22, 2023.
U.S. Appl. No. 17/124,606 Office Action dated Oct. 21, 2022.
Flynn et al., "Correlation and prediction of mass transport across membranes. I. Influence of alkyl chain length on flux-determining properties of barrier and diffusant," J Pharm Sci., Jun. 1972, 61(6):838-52.
International Preliminary Report in Patentability in International Application No. PCT/US2021/025977, dated Oct. 6, 2022, 7 pages.
International Search Report and Written Opinion in International Application No. PCT/US2021/025977, dated Sep. 10, 2021, 10 pages.
Balint et al., 2001, "Activation and activities of the p53 tumour suppressor protein," Br. J. Cancer, vol. 85, pp. 1813-1823.
Bartek et al., 2003, "Chk1 and Chk2 kinases in checkpoint control and cancer," Cancer Cell, vol. 3, pp. 421-429.
Boothroyd et al., "Why Do Some Molecules Form Hydrates or Solvates?" Crystal Growth and Design vol. 18 pp. 1903-1908, 2018.
Braga et al., "Making Crystals from Crystals: a green route to crystal engineering and polymorphism" Chemical Communications (2005) pp. 3635-3645.
Brooks et al., 2012, "A potent chk1 inhibitor is selectively toxic in melanomas with high levels of replicative stress," Oncogene, vol. 32, pp. 788-796.
Carson et al., 1995, "Cancer progression and p53," Lancet, vol. 346, pp. 1009-1011.
Cavelier et al., 2009, "Constitutive activation of the DNA damage signaling pathway in acute myeloid leukemia with complex karyotype: Potential importance for checkpoint targeting therapy," Cancer Res., vol. 69, pp. 8652-8661.
Cole et al., 2011 "RNAi screen of the protein kinome identifies checkpoint kinase 1 (chk1) as a therapeutic target in neuroblastoma," Proc. Natl. Acad. Sci. U.S.A., vol. 108, pp. 3336-3341.
Davies et al., 2011, "Single-agent inhibition of chk1 is antiproliferative in human cancer cell lines in vitro and inhibits tumor xenograft growth in vivo," Oncol. Res., vol. 19, pp. 349-363.
Di Micco et al., 2006, "Oncogene-induced senescence is a DNA damage response triggered by DNA hyper-replication," Nature, vol. 444, pp. 638-642.
Dixon et al., 2002, "Therapeutic exploitation of checkpoint defects in cancer cells lacking p53 function," Cell Cycle 1:6 pp. 362-368.
Durola et al., 2007, "A New Family of Biisoquinoline Chelates", Eur. J. Org. Chem., Issue 1, pp. 125-135.
Extended European Search Report issued in European Patent Application No. 17152400.0, Jun. 2, 2017, 7 pages.
Ferrao et al., 2011, "Efficacy of chk inhibitors as single agents in myc-driven lymphoma cells," Oncogene, vol. 31, pp. 1661-1672.
Gabriel et al., 1908, "Ubergang van der Chinoxalin zur Pyrazinreihe", Berichte der Deutschen Chemischen Gesellschafl, vol. 40, pp. 4850-4860 (with English Abstract).
GB Search Report for GB 0719644.7 dated Apr. 25, 2008.
GB Search Report for GB 0803018.1 dated Jun. 17, 2008.
Greenblatt, M. S., et al. "Mutations in the p53 tumor suppressor gene: clues to cancer etiology and molecular pathogenesis." Cancer Research 54(18) (1994): 4855-4878.
Guzi et al., 2011, "Targeting the replication checkpoint using SCH 900776, a potent and functionally selective CHK1 inhibitor identified via high content screening," Mol. Cancer Ther., vol. 10, pp. 591-602.
Hoglund et al., 2011, "Therapeutic Implications for the Induced Levels of Chkl in Myc-Expressing Cancer Cells, "Clin. Cancer Res., vol. 17 (22), pp. 7067-7079.
Intellectual Property Australia, Examination Report, Australian Patent Application No. 2012335409, Jul. 13, 2016, 2 Pages.
Intellectual Property Australia, Examination Report, Australian Patent Application No. 2013261605, Oct. 5, 2016, 2 Pages.
International Preliminary Report on Patentability for Application No. PCT/GB2013/051233 dated Nov. 18, 2014.
International Preliminary Report on Patentability (IPRP) for PCT/GB2008/002259.
International Preliminary Report on Patentability (IPRP) for PCT/GB2008/003362.
International Preliminary Report on Patentability (IPRP) for PCT/GB2009/000438.
International Preliminary Report on Patentability for PCT-GB2012-052786 dated Jan. 29, 2014.
International Search Report (ISR) and Written Opinion of International Searching Authority (WOISA) for PCT/GB2008/002259.
International Search Report (ISR) and Written Opinion of International Searching Authority (WOISA) for PCT/GB2008/003362.
International Search Report (ISR) and Written Opinion of International Searching Authority (WOISA) for PCT/GB2009/000438.
International Search Report and Written Opinion in International Application No. PCT/GB2013/051233, dated Aug. 6, 2013, 8 pages.
International Search Report for PCT/GB2012/052786 dated Feb. 6, 2013.
Ioannidis et al., "Discovery of pyrazol-3-ylamino pyrazines as novel JAK2 inhibitors", Bioorg. & Med. Chem. Lett., 2009, vol. 19, pp. 6524-6528.
Itoh et al., 2002, "Efficient synthesis of substituted 2-aminopyrazines: FeCl3-promoted condensation of hydroxyiminoketones with aminoacetonitriles", Tetrahedron Lett., vol. 43, pp. 9287-9290.
Jain et al., "Polymorphism in Pharmacy" Indian Drugs (1986) vol. 23 No. 6 pp. 315-329.
Lainchbury et al., 2011, "Checkpoint kinase inhibitors: a patent review (2009-2010)", Exp.Opin. Ther. Pat., vol. 21, No. 8, pp. 1911-1210.

(56) References Cited

OTHER PUBLICATIONS

Lainchbury et al., Oct. 19, 2012, "Discovery of 3-Alkoxyamino-5-(pyridin-2-ylamino)pyrazine-2-carbonitriles as Selective, Orally Bioavailable CHK1 Inhibitors", J. Med. Chem., vol. 55, No. 22, pp. 10229-10240.
Li et al., 2007, "Synthesis and in-vitro biological activity of macrocyclic urea CHK1 inhibitors", Bioorg. & Med. Chem. Lett., vol. 17, pp. 6499-6504.
Lieberman et al., "Pharmaceutical Dosage Forms, vol. 2" Published 1990 by Marcel Dekker, INC, pp. 462-472.
Liu et al., 2000, "Chk1 is an essential kinase that is regulated by Atr and required for the G(2)/M DNA damage checkpoint," Genes Dev., vol. 14, pp. 1448-1459.
Morisette et al., "High-throughput crystallization: polymorphs, salts, co-crystals and solvates of pharmaceutical solids", Advanced Drug Delivery Reviews vol. 56 pp. 275-300, 2004.
Murga et al., 2011, "Exploiting oncogene-induced replicative stress for the selective killing of Myc-driven tumors," Nat. Struct. Mal. Biol., vol. 18, pp. 1331-1335.
Office Action for Japanese Patent Application No. JP 2016-201383, Aug. 15, 2017, 8 Pages, (With English Translation).
Russian Patent Office, Official Action, Russian Patent Application No. 2014121334, Sep. 1, 2016, 6 Pages.
Sanchez et al., 1997, "Conservation of the Chk1 checkpoint pathway in mammals: linkage of DNA damage to Cdk regulation through Cdc25," Science, vol. 277, pp. 1497-1501.
Sorensen et al., 2005, "Cell-cycle checkpoint kinase Chk1 is required for mammalian homologous recombination repair," Nat. Cell Biol., vol. 7, pp. 195-201.
Syljuasen et al., 2015, "Targeting lung cancer through inhibition of checkpoint kinases", Frontiers in Genetics, vol. 6, Article 70, pp. 1-11.
Tao et al., 2006, "Chk1 inhibitors for novel cancer treatment," Anti-Cancer Agents in Medicinal Chemistry, vol. 6, pp. 377-388.
Tao et al., 2007, "Macrocyclic ureas as potent and selective CHK1inhibitors: an improved synthesis, kinome profiling, structure-activity relationships, and preliminary pharmacokinetics," Bioorg. Med. Chem. Lett., vol. 17, pp. 6593-6601.
Tao et al., 2007, "Structure-based design, synthesis, and biological evaluation of potent and selective macrocyclic checkpoint kinase 1 inhibitors," J. Med. Chem., vol. 50, pp. 1514-1527.
Tse et al., 2007, "CHIR-124, a Novel Potent Inhibitor of Chk1, Potentiates the Cyctotoxicity of Topoisomerase | Poisons In vitro and In vivo," Clin. Cancer Res. vol. 13(2) pp. 591-602.
Ugarkar et al., 2000, "Adenosine Kinase Inhibitors. 1. Synthesis, Enzyme Inhibition, and Antiseizure Activity of 5-lodotubercidin Analogues", Journal of Medicinal Chemistry, vol. 43, pp. 2883-2893.
Vippagunta et al., "Crystalline Solids" Advanced Drug Delivery Reviews (2001) vol. 48 pp. 3-26.
Walton et al., 2010, "The Preclinical Pharmacology and Therapeutic Activity of the Novel CHK1 Inhibitor SAR-020106", Molecular Cancer Therapeutics, vol. 9(1), pp. 89-100.
Walton et al., 2012, "CCT244747 Is a Novel Potent and Selective CHK1 Inhibitor with Oral Efficacy Alone and in Combination with Genotoxic Anticancer Drugs", Clin. Cancer Res., vol. 18, pp. 5650-5661.
Wang et al., 1996, "UCN-01: a potent abrogator of G2 checkpoint function in cancer cells with disrupted p53," J. Natl. Cancer Inst., vol. 88, pp. 956-965.
Weinert et al., 1989, "Control of G2 delay by the rad9 gene of Saccharomyces cerevisiae," J. Cell Sci. Suppl., vol. 12, pp. 145-148.
West, "Solid state chemistry and its applications", John Wiley & Sons 2: 584 pages (2022).
White et al., 1967, "Gattermann reaction of 3,5-dimethoxyphenylacetonitrile. Synthesis of 6,8-dioxyisoquinolines", J. Org. Chem., vol. 32, pp. 2689-2692.
Xiao et al., 2006, "Differential roles of checkpoint kinase 1, checkpoint kinase 2, and mitogen-activated protein kinase-48 activated protein kinase 2 in mediating DNA damage-induced cell cycle arrest: implications for cancer therapy," Mol. Cancer Ther., vol. 5, pp. 1935-1943.
Xin et al., "Solvate Prediction for Pharmaceutical Organic Molecules with Machine Learning", Crystal Growth and Design vol. 19 pp. 1903-1911, 2019.
Zachos et al., 2003, "Chk1-deficient tumour cells are viable but exhibit multiple checkpoint and survival defects," EMBO J., vol. 22, pp. 713-723.
Zhao et al., 2002, "Disruption of the checkpoint kinase 1/cell division cycle 25A pathway abrogates ionizing radiation-induced S and G2 checkpoints," Proc. Natl. Acad. Sci. USA, vol. 99, pp. 14795-14800.
Byrn et al., "Pharmaceutical Solids: A strategic Approach to Regulatory Considerations", Pharmaceutical Research, Springer Berlin Heidelberg, Berlin/Heidelberg, vol. 12, No. 7, Jul. 1, 1995, pp. 945-954.
Caira, "Crystalline Polymorphism of Organic Compounds", Topics in Current Chemistry; [Topics in Current Chemistry], Springer, Berlin, DE, vol. 198, Jan. 1, 1998, pp. 163-208.
Liu et al., "Gemcitabine and Chk1 inhibitor AZD7762 synergistically suppress the growth of Lkb1-deficient lung adenocarcinoma." Cancer research 77(18), 5068-5076 (2017).
Wang et al., "Characterization of KRAS rearrangements in metastatic prostate cancer." Cancer Discovery (2011): 35-43.
Zangarini et al., "Development and validation of a LC-MS/MS method for the quantification of the checkpoint kinase 1 inhibitor SRA737 in human plasma." Bioanalysis 9(13), 1001-1010, (2017).

* cited by examiner

METHODS FOR SYNTHESIS OF CHK1 INHIBITORS

CROSS REFERENCE TO RELATED APPLICATIONS

This application is a National Stage Application under 35 U.S.C. § 371 and claims the benefit of International Application No. PCT/US2021/025977, filed Apr. 6, 2021, which claims priority to U.S. Provisional Application No. 63/006,305, filed on Apr. 7, 2020, the disclosure of which is hereby incorporated by reference herein in its entirety.

INTRODUCTION

SRA737 is a heterocyclic small molecule and a potent checkpoint 1 inhibitor that is currently under clinical study as a chemotherapy agent. The structure of SRA737 is:

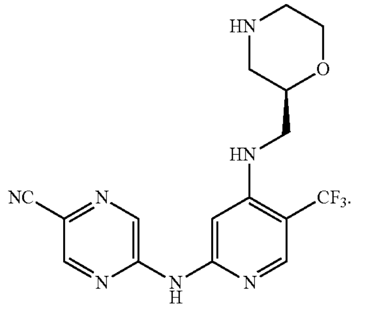 [SMILES: N#Cc1cnc(Nc2cc(NC[C@H]3CNCCO3)c(C(F)(F)F)cn2)cn1]

SRA737 is also known by its IUPAC name: 5-[[4-[[morpholin-2-yl]methylamino]-5-(trifluoromethyl)-2-pyridyl]amino]pyrazine-2-carbonitrile. The existing, conventional synthesis of SRA737 is described in U.S. Pat. No. 9,663,503, which is hereby incorporated by reference in its entirety.

The synthesis of SRA737 and similar heterocyclic compounds currently employs cross-coupling reactions that require high loadings of metal complexes as catalysts and organic phosphine compounds as ligands. While these reactions are essential for rapid construction of molecular complexity, they produce undesired impurities in the intermediates and the final active pharmaceutical ingredient (API) product that are often difficult to purify. Furthermore, these reactions require careful preparations and often harsh reaction conditions, such as elevated temperature and pressure, which can undesirably increase cost for manufacturing.

Due to its molecular complexity, industrial scale manufacturing of SRA737 can be a challenging process. The requirements of multi-step synthesis, purifications, and waste management often lead to low yields of both the intermediates and the final product. Thus, concise and operationally simple synthetic processes for large scale manufacturing of SRA737 and related heterocyclic small molecules are highly desirable. There is a high demand for improved synthetic processes to produce heterocyclic compounds, such as SRA737, on industrial scales with improved atom economy, waste management, and purification process to reduce manufacturing cost.

SUMMARY

The present disclosure provides novel compounds, compositions, and methods of making such compounds and compositions.

In some embodiments, the compounds disclosed herein are novel synthetic intermediates of SRA737. In some embodiments, the compounds are protected forms of SRA737, that is, the compound is masked with a protecting organic group that, when exposed to appropriate conditions, is removed to produce SRA737.

In some embodiments, the present disclosure provides novel compositions, compounds and solvates comprising very low concentrations of palladium impurities. In some embodiments, the compound is an active pharmaceutical ingredient (API) compound.

In some embodiments, the present disclosure provides novel compositions, compounds and solvates comprising very low concentrations of other organic compounds as impurities, i.e. side-products from a given reaction or cumulative reactions to a given point in the total synthesis of SRA737.

In some embodiments, the present disclosure provides novel synthetic intermediates and SRA737, or protected forms of SRA737 that are substantially free of palladium and other organic molecules as impurities.

In some embodiments, the present disclosure provides compositions of one or more compounds disclosed herein that are substantially free of palladium and other organic molecules as impurities.

In some embodiments, the present disclosure provides compositions comprising a novel synthetic intermediate compound and/or SRA737, or protected forms of SRA737, that are substantially free of palladium and other organic molecules as impurities.

In some embodiments, the compounds disclosed herein are novel solvates. In some embodiments, the compounds disclosed herein are novel dimethylformamide (DMF) solvates. In some embodiments, the compounds disclosed herein are novel crystalline solids. In some embodiments, the compounds disclosed herein are novel crystalline solids that are substantially free of palladium and other organic molecules as impurities.

In some embodiments, the present disclosure provides pharmaceutical compositions comprising one or more compounds or solvates.

In some embodiments, the present disclosure provides a kit comprising one or more compounds disclosed herein, or one or more compositions as disclosed herein.

In some embodiments, the present disclosure provides methods of administering to a subject in need of chemotherapy at least one of the compounds described herein.

In some embodiments, the present disclosure provides methods of manufacturing novel compounds, compositions and solvates.

These and other embodiments are described in further detail herein.

DETAILED DESCRIPTION

Definitions

Figure 1:
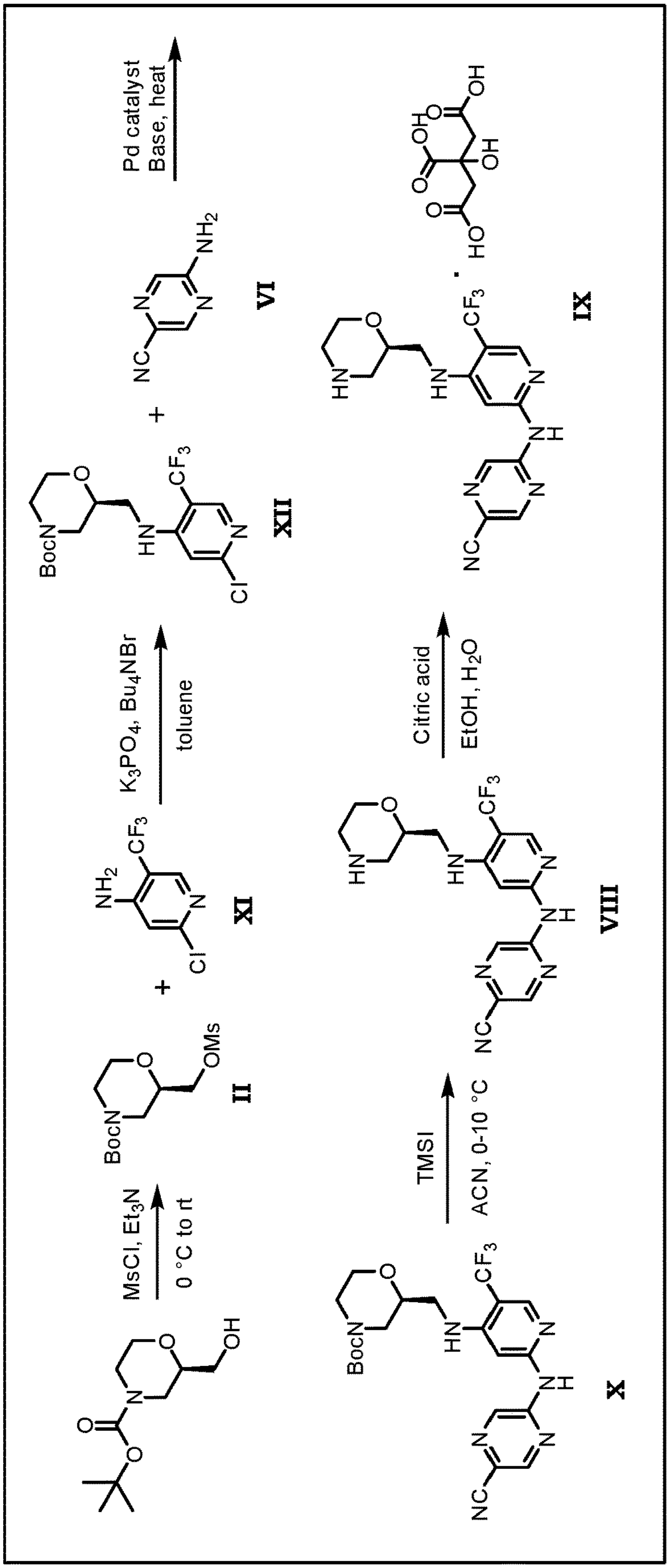
FIG. 1 shows a total synthesis of SRA737.

Various terms used in the specification and claims herein are defined as set forth below. All technical and scientific terms not defined herein have the meaning commonly understood by a person skilled in the art to which this invention belongs.

"LvG" or "Leaving group" has the meaning conventionally associated with it in synthetic organic chemistry and refers to an atom or organic group which is capable of being displaced from a molecule by a nucleophile via covalent bond cleavage. Exemplary leaving groups include, but are not limited to: F, Cl, Br, I, OTs ($—OSO_2C_6H_4CH_3$), OMs ($—OSO_2CH_3$), ONs ($SO_2C_6H_4NO_2$), OTf ($—OSO_2CF_3$), $N_2^+$, $H_2O^+$, carbonates ($—OCO_2R$), esters (—OCOR), acid (—OCOH), and anhydrides ($—OCO_2COR$).

"Substantially purified or free of impurities" refers to a mixture in which one small organic molecule of interest far exceeds the amount of minerals, metal, and/or other small organic molecules as impurities, and at least 95% by dry weight is the small organic molecule of interest, such as at least 96%, at least 97%, at least 98%, at least 99% or at least 99.5% by dry weight.

It is understood that it may be desirable to protect certain reactive groups or substituents (e.g., amino groups) during some of the procedures described herein. Any convenient protection and deprotection methods and chemistries can be utilized in conjunction with such reactive groups or substituents. "Amino protecting group" refers to an organic group that can be covalently attached to a reactive amino group to block undesirable reactions and is capable of being selectively removed from the amino group using a deprotection method. The choice and use of protecting groups and the reaction conditions to install and remove protecting groups include those described in Greene's Protective Groups in Organic Synthesis, 4th edition, John Wiley & Sons, New York, 2007, the disclosure of which is incorporated herein by reference in its entirety. Exemplary amino protecting groups include, but are not limited to, TMS, TBDMS, TBDPS, Ms, Ns, Tf, Fmoc, Boc, Cbz, Troc, Alloc, acetyl

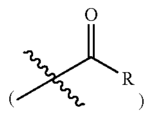

including acetamide where R=methyl or trifluoroacetamide where R=trifluouromethyl, hydroxylamine

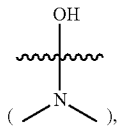

Tr or trityl ($—C(Ph)_3$), benzylidene

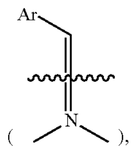

hydrazinyl

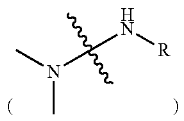

where R also can be C(O)R', benzoyl (—C(O)Ph), benzyl ($—CH_2Ph$), allyl, vinyl, $Bu^t$, and Piv.

"Alkyl" refers to monovalent saturated aliphatic hydrocarbyl groups having from 1 to 20 carbon atoms, such as 1-12 carbons. This term includes, by way of example, linear and branched hydrocarbyl groups such as methyl ($CH_3—$), ethyl ($CH_3CH_2—$), n-propyl ($CH_3CH_2CH_2—$), isopropyl ($(CH_3)_2CH—$), n-butyl ($CH_3CH_2CH_2CH_2—$), isobutyl ($(CH_3)_2CHCH_2—$), sec-butyl ($(CH_3)(CH_3CH_2)CH—$), t-butyl ($(CH_3)_3C—$), n-pentyl ($CH_3CH_2CH_2CH_2CH_2—$), and neopentyl ($(CH_3)_3CCH_2—$). $C_x$ alkyl refers to an alkyl group having x number of carbon atoms.

"Alkenyl" refers to straight or branched hydrocarbyl groups having from 1 to 12 carbon atoms and preferably 2 to 4 carbon atoms and having at least 1 and preferably from 1 to 2 sites of unsaturation (>C=C<). Such groups are exemplified, for example, by vinyl, allyl, and but-3-en-1-yl. Included within this term are the cis and trans isomers or mixtures of these isomers. $C_x$ alkenyl refers to an alkenyl group having x number of carbon atoms.

"Alkynyl" refers to straight or branched monovalent hydrocarbyl groups having from 2 to 6 carbon atoms and preferably 2 to 3 carbon atoms and having at least 1 and preferably from 1 to 2 sites of acetylenic (—C≡C—) unsaturation. Examples of such alkynyl groups include acetylenyl (—C≡CH), and propargyl ($—CH_2C≡CH$). $C_x$ alkynyl refers to an alkynyl group having x number of carbon atoms.

"Substituted alkyl" refers to an alkyl group having from 1 to 5, preferably 1 to 3, or more preferably 1 to 2 substituents selected from the group consisting of alkoxy, substituted alkoxy, acyl, acylamino, aminocarbonylamino, acyloxy, amino, substituted amino, aminocarbonyl, aminothiocarbonyl, aminocarbonylamino, aminothiocarbonylamino, aminocarbonyloxy, aminosulfonyl, aminosulfonyloxy, aminosulfonylamino, amidino, aryl, substituted aryl, aryloxy, substituted aryloxy, arylthio, substituted arylthio, carboxyl, carboxyl ester, (carboxyl ester)amino, (carboxyl ester)oxy, cyano, cycloalkyl, substituted cycloalkyl, cycloalkyloxy, substituted cycloalkyloxy, cycloalkylthio, substituted cycloalkylthio, guanidino, substituted guanidino, halo, hydroxy, heteroaryl, substituted heteroaryl, heteroaryloxy, substituted heteroaryloxy, heteroarylthio, substituted heteroarylthio, heterocyclic, substituted heterocyclic, heterocyclyloxy, substituted heterocyclyloxy, heterocyclylthio, substituted heterocyclylthio, nitro, $SO_3H$, substituted sulfonyl, sulfonyloxy, thioacyl, thiol, alkylthio, and substituted alkylthio, wherein said substituents are defined herein.

In some embodiments, the substituted alkyl groups include halogenated alkyl groups and particularly halogenated methyl groups such as trifluoromethyl, difluoromethyl, fluoromethyl and the like.

"Alkyl aryl" refers to an alkyl group having from 1 to 8, preferably 1 to 5, or more preferably 1 to 3 carbon atoms in length and is substituted specifically at any one of the carbons along the chain with an aryl group.

"Alkenyl aryl" refers to an alkenyl or alkene group having from 1 to 8, preferably 1 to 5, or more preferably 1 to 3 carbon atoms in length and is substituted specifically at any one of the carbons along the chain with an aryl group. The aryl group can include heteroatoms or not.

"Alkynyl aryl" refers to an alkynyl or alkyne group having from 1 to 8, preferably 1 to 5, or more preferably 1 to 3 carbon atoms in length and is substituted specifically at any one of the carbons along the chain with an aryl group. The aryl group can include heteroatoms or not.

"Cycloalkyl" or "Cyclyl alkyl" refers to a saturated or partially saturated, but not aromatic, group having from 3 to 10 ring carbon atoms and no heteroatoms. Cycloalkyl encompasses single ring systems.

"Ar" and/or "aryl" refers to any group which is aromatic. This group must be cyclic; and does not contain heteroatoms.

"Alkoxy" refers to the group —O-alkyl wherein alkyl is defined herein. Alkoxy includes, by way of example, methoxy, ethoxy, n-propoxy, isopropoxy, n-butoxy, t-butoxy, sec-butoxy, and n-pentoxy.

"Substituted alkoxy" refers to the group —O-(substituted alkyl) wherein substituted alkyl is defined herein. Preferred substituted alkyl groups in —O-(substituted alkyl) include halogenated alkyl groups and particularly halogenated methyl groups such as trifluoromethyl, difluoromethyl, fluoromethyl and the like.

"Acyl" refers to the groups H—C(O)—, alkyl-C(O)—, substituted alkyl-C(O)—, alkenyl-C(O)—, substituted alkenyl-C(O)—, alkynyl-C(O)—, substituted alkynyl-C(O)—, cycloalkyl-C(O)—, substituted cycloalkyl-C(O)—, aryl-C(O)—, substituted aryl-C(O)—, heteroaryl-C(O)—, substituted heteroaryl-C(O)—, heterocyclic-C(O)—, and substituted heterocyclic-C(O)—, wherein alkyl, substituted alkyl, alkenyl, substituted alkenyl, alkoxy, substituted alkoxy, alkynyl, substituted alkynyl, cycloalkyl, substituted cycloalkyl, aryl, substituted aryl, heteroaryl, substituted heteroaryl, heterocyclic and substituted heterocyclic are as defined herein. Acyl includes the "acetyl" group $CH_3C(O)$—.

"Acylamino" refers to the groups —NRC(O)alkyl, —NRC(O) substituted alkyl, —NRC(O)cycloalkyl, substituted —NRC(O) cycloalkyl, —NRC(O)alkenyl, substituted —NRC(O) alkenyl, alkoxy, substituted alkoxy-$NR^AC(O)$ alkynyl, substituted —NRC(O) alkynyl, —NRC(O)aryl, substituted —NRC(O) aryl, —NRC(O)heteroaryl, substituted —NRC(O) heteroaryl, —NRC(O)heterocyclic, and substituted —NRC(O) heterocyclic wherein R is hydrogen or alkyl, and wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic and substituted heterocyclic are as defined herein.

"Acyloxy" refers to the groups alkyl-C(O)O—, substituted alkyl-C(O)O—, alkenyl-C(O)O—, substituted alkenyl-C(O)O—, alkynyl-C(O)O—, substituted alkynyl-C(O)O—, aryl-C(O)O—, substituted aryl-C(O)O—, cycloalkyl-C(O)O—, substituted cycloalkyl-C(O)O—, heteroaryl-C(O)O—, substituted heteroaryl-C(O)O—, heterocyclic-C(O)O—, and substituted heterocyclic-C(O)O— wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic, and substituted heterocyclic are as defined herein.

"Amino" refers to the group —$NH_2$.

"Aminocarbonyl" refers to the group —$C(O)NR^AR^A$ where $R^A$ and $R^B$ are independently selected from the group consisting of hydrogen, alkyl, substituted alkyl, alkenyl, substituted alkenyl, alkoxy, substituted alkoxy, alkynyl, substituted alkynyl, aryl, substituted aryl, cycloalkyl, substituted cycloalkyl heteroaryl, substituted heteroaryl, heterocyclic, and substituted heterocyclic and where $R^A$ and $R^B$ are optionally joined together with the nitrogen bound thereto to form a heterocyclic or substituted heterocyclic group, and wherein alkyl, substituted alkyl, alkenyl, substituted alkenyl, alkoxy, substituted alkoxy, alkynyl, substituted alkynyl, cycloalkyl, substituted cycloalkyl, aryl, substituted aryl, heteroaryl, substituted heteroaryl, heterocyclic and substituted heterocyclic are as defined herein.

"Substituted aryl" refers to aryl groups which are substituted with 1 to 5, preferably 1 to 3, or more preferably 1 to 2 substituents selected from the group consisting of alkyl, substituted alkyl, alkenyl, substituted alkenyl, alkynyl, substituted alkynyl, alkoxy, substituted alkoxy, acyl, acylamino, aminocarbonylamino, acyloxy, amino, substituted amino, aminocarbonyl, aminothiocarbonyl, aminocarbonylamino, aminothiocarbonylamino, aminocarbonyloxy, aminosulfonyl, aminosulfonyloxy, aminosulfonylamino, amidino, aryl, substituted aryl, aryloxy, substituted aryloxy, arylthio, substituted arylthio, carboxyl, carboxyl ester, (carboxyl ester) amino, (carboxyl ester)oxy, cyano, cycloalkyl, substituted cycloalkyl, cycloalkyloxy, substituted cycloalkyloxy, cycloalkylthio, substituted cycloalkylthio, guanidino, substituted guanidino, halo, hydroxy, heteroaryl, substituted heteroaryl, heteroaryloxy, substituted heteroaryloxy, heteroarylthio, substituted heteroarylthio, heterocyclic, substituted heterocyclic, heterocyclyloxy, substituted heterocyclyloxy, heterocyclylthio, substituted heterocyclylthio, nitro, $SO_3H$, substituted sulfonyl, sulfonyloxy, thioacyl, thiol, alkylthio, a monosaccharide (which may be covalently bonded to the aryl group thru any oxygen atom on the saccharide), and substituted alkylthio, wherein said substituents are defined herein.

"Carbonyl" refers to the divalent group —C(O)— which is equivalent to —C(=O)—.

"Carboxy" or "carboxyl" refers to —COOH or salts thereof.

"Carboxyl ester" or "carboxy ester" refers to the groups —C(O)O-alkyl, —C(O)O-substituted alkyl, —C(O)O-alkenyl, —C(O)O-substituted alkenyl, —C(O)O-alkynyl, —C(O)O-substituted alkynyl, —C(O)O-aryl, —C(O)O-substituted aryl, —C(O)O-cycloalkyl, —C(O)O-substituted cycloalkyl, —C(O)O-heteroaryl, —C(O)O-substituted heteroaryl, —C(O)O-heterocyclic, and —C(O)O-substituted heterocyclic wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic, and substituted heterocyclic are as defined herein.

"Cyano" refers to the group —C≡N.

"Cycloalkyl" refers to a saturated or unsaturated but nonaromatic cyclic alkyl groups of from 3 to 10 carbon atoms having single or multiple cyclic rings including fused, bridged, and spiro ring systems. $C_x$ cycloalkyl refers to a cycloalkyl group having x number of ring carbon atoms. Examples of suitable cycloalkyl groups include, for instance, adamantyl, cyclopropyl, cyclobutyl, cyclopentyl, and cyclooctyl. One or more the rings can be aryl, heteroaryl, or heterocyclic provided that the point of attachment is through the non-aromatic, non-heterocyclic ring saturated carbocyclic ring.

"Substituted cycloalkyl" refers to a cycloalkyl group having from 1 to 5 or preferably 1 to 3 substituents selected from the group consisting of oxo, thione, alkyl, substituted alkyl, alkenyl, substituted alkenyl, alkynyl, substituted alkynyl, alkoxy, substituted alkoxy, acyl, acylamino, aminocarbonylamino, acyloxy, amino, substituted amino, aminocarbonyl, aminothiocarbonyl, aminocarbonylamino, aminothiocarbonylamino, aminocarbonyloxy, aminosulfonyl, aminosulfonyloxy, aminosulfonylamino, amidino, aryl, substituted aryl, aryloxy, substituted aryloxy, arylthio, substituted arylthio, carboxyl, carboxyl ester, (carboxyl ester) amino, (carboxyl ester)oxy, cyano, cycloalkyl, substituted cycloalkyl, cycloalkyloxy, substituted cycloalkyloxy, cycloalkylthio, substituted cycloalkylthio, guanidino, substituted guanidino, halo, hydroxy, heteroaryl, substituted heteroaryl, heteroaryloxy, substituted heteroaryloxy, heteroarylthio, substituted heteroarylthio, heterocyclic, substituted heterocyclic, heterocyclyloxy, substituted heterocyclyloxy, heterocyclylthio, substituted heterocyclylthio, nitro, $SO_3H$, substituted sulfonyl, sulfonyloxy, thioacyl, thiol, alkylthio, and substituted alkylthio, wherein said substituents are defined herein.

"Halo" or "halogen" refers to fluoro, chloro, bromo and iodo and preferably is fluoro or chloro.

"Hydroxy" or "hydroxyl" refers to the group —OH.

"Heteroaryl" refers to an aromatic group of from 4 to 10 carbon atoms and 1 to 4 heteroatoms selected from the group consisting of oxygen, nitrogen and sulfur within the ring. Such heteroaryl groups can have a single ring (e.g., pyridinyl or furyl) or multiple condensed rings (e.g., indolizinyl or benzothienyl) wherein the condensed rings may or may not be aromatic and/or contain a heteroatom provided that the point of attachment is through an atom of the aromatic heteroaryl group. In one embodiment, the nitrogen and/or the sulfur ring atom(s) of the heteroaryl group are optionally oxidized to provide for the N-oxide (N→O), sulfinyl, or sulfonyl moieties. Preferred heteroaryls include 5 or 6 membered heteroaryls such as pyridinyl, pyrrolyl, indolyl, thiophenyl, and furanyl.

"Substituted heteroaryl" refers to heteroaryl groups that are substituted with from 1 to 5, preferably 1 to 3, or more preferably 1 to 2 substituents selected from the group consisting of the same group of substituents defined for substituted aryl.

"Heterocycle" or "heterocyclic" or "heterocycloalkyl" or "heterocyclyl" refers to a saturated or partially saturated, but not aromatic, group having from 2 to 10 ring carbon atoms and from 1 to 4 ring heteroatoms selected from the group consisting of nitrogen, sulfur, or oxygen. $C_x$ cycloalkyl or heterocycloalkyl refers to a group having x number of ring carbon atoms excluding the ring heteroatoms. Heterocycle encompasses single ring or multiple condensed rings, including fused, bridged and spiro ring systems. In fused ring systems, one or more the rings can be cycloalkyl, aryl or heteroaryl provided that the point of attachment is through the non-aromatic ring. In one embodiment, the nitrogen and/or sulfur atom(s) of the heterocyclic group are optionally oxidized to provide for the N-oxide, sulfinyl, sulfonyl moieties.

"Substituted heterocyclic" or "substituted heterocycloalkyl" or "substituted heterocyclyl" refers to heterocyclyl groups that are substituted with from 1 to 5 or preferably 1 to 3 of the same substituents as defined for substituted cycloalkyl. Examples of heterocycle and heteroaryl include, but are not limited to, azetidine, pyrrole, imidazole, pyrazole, pyridine, pyrazine, pyrimidine, pyridazine, indolizine, isoindole, indole, dihydroindole, dexahydroindole, dihydropyridine, indazole, purine, quinolizine, isoquinoline, quinoline, phthalazine, naphthylpyridine, quinoxaline, quinazoline, cinnoline, pteridine, carbazole, carboline, phenanthridine, acridine, phenanthroline, isothiazole, phenazine, isoxazole, phenoxazine, phenothiazine, imidazolidine, imidazoline, imidazolinone, piperidine, piperazine, indoline, phthalimide, 1,2,3,4-tetrahydroisoquinoline, 4,5,6,7-tetrahydrobenzo[b]thiophene, thiazole, thiazolidine, thiophene, benzo[b]thiophene, morpholinyl, thiomorpholinyl (also referred to as thiamorpholinyl), 1,1-dioxothiomorpholinyl, piperidinyl, pyrrolidine, and tetrahydrofuranyl.

The term "salt" or "pharmaceutically acceptable salt" refers to a salt which is acceptable for administration to a subject. It is understood that such salts, with counter ions, will have acceptable mammalian safety for a given dosage regime. Such salts can also be derived from pharmaceutically acceptable inorganic or organic bases and from pharmaceutically acceptable inorganic or organic acids, and may comprise organic and inorganic counter ions. The neutral forms of the compounds described herein may be converted to the corresponding salt forms by contacting the compound with a base or acid and isolating the resulting salts. Examples of salts include, but are not limited to: acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, fumarate, flucoheptanoate, glycerophosphate, hemisulfate, heptanoate, hexanoate, hydrochloride, hydrobromide, hydroiodide, 2-hydroxyethanesulfonate, lactate, maleate, methanesulfonate, 2-naphthalenesulfonate, nicotinate, oxalate, palmoate, pectinate, persulfate, phenylpropionate, picrate, pivalate, propionate, succinate, tartrate, thiocyanate, tosylate, undecanoate, and the like.

Other examples of salts include anions of the compounds of the present disclosure compounded with a suitable cation such as N+, NH4+, and NW4+ (where W can be a C1-C8 alkyl group), and the like. For therapeutic use, salts of the compounds of the present disclosure can be pharmaceutically acceptable. However, salts of acids and bases that are non-pharmaceutically acceptable may also find use, for example, in the preparation or purification of a pharmaceutically acceptable compound.

"Substitution" or "substitution" or "substituted" generally refers groups which are covalently bonded to an atom to replace a hydrogen atom. The atom in this general context can be a carbon atom or a heteroatom, for example a nitrogen atom.

"Tautomer" refers to alternate forms of a compound that differ in the position of a proton, such as enol-keto and imine-enamine tautomers, or the tautomeric forms of heteroaryl groups containing a ring atom attached to both a ring NH moiety and a ring=N moiety such as pyrazoles, imidazoles, benzimidazoles, triazoles, and tetrazoles.

The term "ameliorating" refers to any therapeutically beneficial result in the treatment of a disease state, e.g., a cellular proliferation disease state, including lessening in the severity or progression, remission, or cure thereof.

The term "mammal" includes both humans and non-humans and include but is not limited to humans, non-human primates, canines, felines, murines, bovines, equines, and porcines.

The term "therapeutically effective amount" is an amount that is effective to ameliorate a symptom of a disease. A therapeutically effective amount can, in some embodiments, be a "prophylactically effective amount" as prophylaxis can be considered therapy.

"Subject" refers to a mammalian organism treated using a compound of the present invention. The "subject" can be a human or non-human mammalian organism.

"Treating" or "treatment" of a disease or disorder in a subject refers to ameliorating the disease, as defined above.

An agent is said to be "specific" if it reacts or associates more frequently, more rapidly, with greater duration and/or with greater affinity with a specified target than it does with alternative substances, especially as compared to substances that are structurally related to the target, e.g., an isoform of the target. In some embodiments, an agent is "specific" for a target if a concentration of the agent that produces a maximal effect in an in vitro or in vivo target assay (e.g., a binding assay or an enzyme activity assay) produces no measurable effect in a comparable assay carried out using another substance, especially one or more substances that are structurally related to the target.

The term "contacting" includes both directly contacting cells, for example, in vivo, in vitro, or ex vivo, or indirectly contacting cells, such as, for example, by administering an agent to a subject. Further, "contacting" a cell with an agent includes administering or applying a prodrug version of the agent.

The terms "prevent," "preventing," "prevention," "prophylactic treatment" and the like refer to reducing the probability of developing a disease, disorder, or condition in a subject, who does not have, but is at risk of or susceptible to developing a disease, disorder, or condition. Thus, in some embodiments, an agent can be administered prophylactically to prevent the onset of a disease, disorder, or condition, or to prevent the recurrence of a disease, disorder, or condition.

The term "mol %" refers to the percentage of the total moles of a particular component as compared to the limiting reagent of any given reaction The term "wt %" refers to the weight percent of a particular component within a solution.

The term "ppm" refers to parts per million.

Additional Interpretational Conventions

Generally, reference to or depiction of a certain element such as hydrogen or H is meant to include all isotopes of that element. For example, if an R group is defined to include hydrogen or H, it also includes deuterium and tritium. Compounds comprising radioisotopes such as tritium, $^{14}C$, $^{32}P$ and $^{35}S$ are thus within the scope of the present technology. Procedures for inserting such labels into the compounds of the present technology will be readily apparent to those skilled in the art based on the disclosure herein.

Unless the specific stereochemistry is expressly indicated, all chiral, diastereomeric, and racemic forms of a compound are intended. Thus, compounds described herein include enriched or resolved optical isomers at any or all asymmetric atoms as are apparent from the depictions. Racemic mixtures, and d or l enriched stereomeric mixtures, as well as the individual optical isomers can be isolated or synthesized so as to be substantially free of their enantiomeric or diastereomeric partners, and these stereoisomers are all within the scope of the present technology.

The compounds described herein may exist as solvates, especially hydrates, and unless otherwise specified, all such solvates and hydrates are intended. Hydrates may form during manufacture of the compounds or compositions comprising the compounds, or hydrates may form over time due to the hygroscopic nature of the compounds. Compounds of the present technology may exist as organic solvates as well, including DMF, ether, and alcohol solvates, among others. The identification and preparation of any particular solvate is within the skill of the ordinary artisan of synthetic organic or medicinal chemistry.

It is understood that the definitions presented herein are not intended to include impermissible substitution patterns (e.g., methyl substituted with 5 fluoro groups). Such impermissible substitution patterns are well known to the skilled artisan.

Throughout this application, the text refers to various embodiments of the present compounds, compositions, and methods. The various embodiments described are meant to provide a variety of illustrative examples and should not be construed as descriptions of alternative species. Rather, it should be noted that the descriptions of various embodiments provided herein may be of overlapping scope. The embodiments discussed herein are merely illustrative and are not meant to limit the scope of the present technology.

Singular articles such as "a," "an" and "the" and similar referents in the context of describing the elements (especially in the context of the following claims) are to be construed to cover both the singular and the plural, unless otherwise indicated herein or clearly contradicted by context. Recitation of ranges of values herein are merely intended to serve as a shorthand method of referring individually to each separate value falling within the range, including the upper and lower bounds of the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the embodiments and does not pose a limitation on the scope of the claims unless otherwise stated. No language in the specification should be construed as indicating any non-claimed element as essential.

Unless indicated otherwise, the nomenclature of substituents that are not explicitly defined herein are arrived at by naming the terminal portion of the functionality followed by the adjacent functionality toward the point of attachment. For example, the substituent "alkoxycarbonylalkyl" refers to the group (alkoxy)-C(O)-(alkyl)-.

Processes

In a first aspect, the present disclosure provides a process of manufacture of SRA737 (compound formula VIII). In some embodiments, the disclosure provides for a process of manufacturing SRA737 wherein the process returns an amount of SRA737 greater than or equivalent to five hundred (500) grams. In some embodiments, the present disclosure provides for a process of manufacturing SRA737 wherein the process returns an amount of SRA737 greater than or equivalent to one (1) kilogram of SRA737. In some embodiments, the present disclosure provides for a process of manufacturing novel synthetic intermediates useful for the total synthesis of SRA737.

I. Crystallization

In some embodiments, the present disclosure provides for a process of crystallizing a compound or a salt.

In some embodiments, a process of crystallization is used to purify a compound from a mixture after a coupling step.

In some embodiments, a process of crystallization is used to purify a compound from a mixture after a deprotection step.

In some embodiments, a process of crystallization is used to purify a salt from a mixture.

In some embodiments, a process of crystallization is used to isolate a compound from a mixture after a coupling step.

In some embodiments, a process of crystallization is used to isolate a compound from a mixture after a deprotection step.

In some embodiments, a process of crystallization is used to isolate a salt from a mixture.

In some embodiments, a process of crystallization comprises the addition of water, an acid, or an alcohol to the mixture.

In some embodiments, a process of crystallization comprises maintaining the temperature of the mixture at about −78° C., about −15° C., about 0° C., about 10° C., about 20° C., about 30° C., about 40° C., or about 50° C.

II. Coupling Reaction

In some embodiments, the present disclosure provides for a process of coupling two heterocyclic compounds, each of which contain one or more nitrogen atoms.

In some embodiments, the present disclosure provides a process of coupling two heterocyclic compounds together. In some embodiments, the process couples two heterocyclic compounds, each of which contain one or more nitrogen atoms.

In some embodiments, the coupling is carried out in the presence of relatively low concentrations of metal catalysts, for example about 0.01 to about 0.3 mol %, and ligand additive, for example about 0.01 to about 0.4 mol %.

In some embodiments, the disclosure provides a process comprising:

a) coupling a compound of formula A:

A

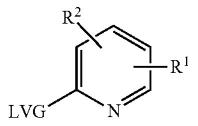

with a compound of formula B:

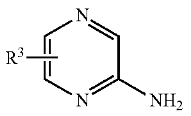

under cross coupling reaction conditions to form a compound of formula C:

C

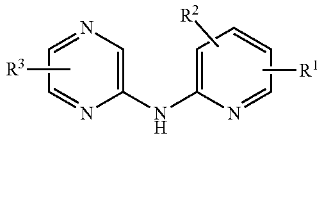

;

and b) crystallizing and isolating the compound of formula C from the reaction mixture of step a);

wherein $R^1$ and $R^2$ are independently selected from: $C_{1-12}$ alkyl, substituted $C_{1-12}$ alkyl, $C_{1-12}$ alkenyl, substituted $C_{1-12}$ alkenyl, $C_{1-12}$ alkynyl, substituted $C_{1-12}$ alkynyl, $C_{1-12}$ alkoxy, substituted $C_{1-12}$ alkoxy, amino, substituted amino, $C_{3-8}$ cycloalkyl, and substituted $C_{3-8}$ cycloalkyl;

and wherein $R^3$ is selected from: cyano, halogen, nitro, carboxy ester and acylamino.

In some embodiments, the cross coupling reaction conditions further comprise:

a) providing a first mixture comprising a compound of formula A, a compound of formula B, a catalyst, a ligand and DMF;

b) providing a second mixture comprising an inorganic base and DMF, wherein the second mixture has been heated to between about 125-135° C.;

c) contacting the first mixture with the second mixture to provide a third mixture, wherein the temperature of the third mixture is maintained between about 125-135° C. for a period of time sufficient to produce a compound of formula C.

In some embodiments, a process of crystallization is used to purify a compound from a mixture after the cross coupling step.

In some embodiments, a process of crystallization is used to isolate a compound from a mixture after the cross coupling step.

In some embodiments, the process provides cross coupling reaction conditions comprising a palladium compound, an organophosphorus compound, an inorganic base, and a polar aprotic organic solvent.

In some embodiments, the process provides cross coupling reaction conditions wherein the amount of palladium is no more than about 0.3 mol %.

In some embodiments, the process provides cross coupling reaction conditions wherein the amount of palladium is no more than about 0.25 mol %.

In some embodiments, the process provides cross coupling reaction conditions wherein the amount of palladium is no more than about 0.2 mol %.

In some embodiments, the process provides cross coupling reaction conditions wherein the amount of palladium is no more than about 0.15 mol %.

In some embodiments, the process provides cross coupling reaction conditions wherein the amount of palladium is no more than about 0.1 mol %.

In some embodiments, the process provides cross coupling reaction conditions comprising an organophosphorus compound wherein the organophosphorus compound is selected from the group consisting of: 2-Dicyclohexylphosphino-2',6'-dimethoxybiphenyl (SPhos), XPhos [2-Dicyclohexylphosphino-2',4',6'-triisopropylbiphenyl], 2-Di-tert-butylphosphino-2',4',6'-triisopropylbiphenyl (tBuXPhos), CyJohnPhos [(2-Biphenyl)dicyclohexylphosphine], DavePhos [2-Dicyclohexylphosphino-2'-(N,N-dimethylamino) biphenyl], JohnPhos [(2-Biphenyl)di-tert-butylphosphine, (2-Biphenylyl)di-tert-butylphosphine, 2-(Di-tert-butylphosphino)biphenyl], MePhos [2-Dicyclohexylphosphino-2'-methylbiphenyl, 2-Methyl-2'-dicyclohexylphosphinobiphenyl, MebiphPCy2], Me4tButylXphos [2-Di-tert-butylphosphino-3,4,5,6-tetramethyl-2',4',6'-triisopropyl-1,1'-biphenyl], PhDave-Phos [2'-(Diphenylphosphino)-N,N'-dimethyl-(1,1'-biphenyl)-2-amine], SPhos [2-Dicyclohexylphosphino-2',6'-dimethoxybiphenyl], RuPhos [2-Dicyclohexylphosphino-2',6'-diisopropoxybiphenyl], sSPhos [Sodium 2'-dicyclohexylphosphino-2,6-dimethoxy-1,1'-biphenyl-3-sulfonate], tBuMePhos [2-Di-tert-butylphosphino-2'-methylbiphenyl], 2-Di-tert-butylphosphino-2',4',6'-triisopropylbiphenyl, (tert-Butyl XPhos), 2-Di-tert-butylphosphino-3,4,5,6-tetramethyl-2',4',6'-triisopropyl-1,1'-biphenyl, 2-Di-tert-butylphosphino-2'-(N,N-dimethylamino)biphenyl (tBuDavePhos), 2-(Dicyclohexylphosphino)biphenyl (Cyclohexyl JohnPhos), 2-Dicyclohexylphosphino-2',6'-diisopropoxybiphenyl, 2-Diphenylphosphino-2'-(N,N-dimethylamino)biphenyl (PhDavePhos), sodium 2-dicyclohexylphosphino-2',6'-dimethoxybiphenyl-3'-sulfonate, 2-(Dicyclohexylphosphino) 3,6-dimethoxy-2',4',6'-triisopropyl-1,1'-biphenyl (BrettPhos), Di-admantyl BrettPhos-2-(Diadamantylphosphino)3,6-dimethoxy-2',4',6'-triisopropyl-1,1'-biphenyl [AdBrettPhos], (2-Di-tert-butylphosphino-3-methoxy-6-methyl-2',4',6'-triisopropyl-1,1'-biphenyl) [RockPhos], 2-(Di-tert-butylphosphino)-2',4',6'-triisopropyl-3,6-dimethoxy-1,1'-biphenyl, [t-Bu Brett Phos] or Josiphos [(R) or (S)-1-[(SP)-2-(Dicyclohexylphosphino)ferrocenyl]ethyldi-tert-butylphosphine].

In some embodiments, the process provides cross coupling reaction conditions comprising an organophosphorus compound wherein the organophosphorus compound is selected from the group consisting of: 2-(Di-tert-butylphosphino)-2',4',6'-triisopropyl-3,6-dimethoxy-1,1'-biphenyl, [t-Bu Brett Phos], [(1,3,5,7-Tetramethyl-6-phenyl-2,4,6-trioxa-6-phosphaadamantane)-2-(2'-amino-1,1'-biphenyl)], and [(di(1-adamantyl)-n-butylphosphine)-2-(2'-amino-1,1'-biphenyl)] [cataCXium-A].

In some embodiments, the process provides cross coupling reaction conditions comprising an organophosphorus compound wherein the organophosphorus compound is cataCXium-A [(di(1-adamantyl)-n-butylphosphine)-2-(2'-amino-1,1'-biphenyl)].

In some embodiments, the process provides cross coupling reaction conditions comprising an organophosphorus compound wherein the organophosphorus compound is Josiphos [(R) or (S)-1-[(SP)-2-(Dicyclohexylphosphino)ferrocenyl]ethyldi-tert-butylphosphine].

In some embodiments, the process provides cross coupling reaction conditions comprising a palladium compound wherein the palladium compound is [2-(2'-amino-1,1'-biphenyl)] palladium(II) methanesulfonate. In some embodiments, the process provides cross coupling reaction conditions comprising a palladium compound wherein the palladium compound is [2-(2'-methylamino-1,1'-biphenyl)] palladium(II) methanesulfonate (i.e. there is a methyl group on the nitrogen atom).

In some embodiments, the process provides cross coupling reaction conditions comprising a palladium compound wherein the palladium compound is $Pd(dba)_2$ [Bis(dibenzylideneacetone) palladium(O)].

In some embodiments, the process provides cross coupling reaction conditions comprising a palladium compound wherein the palladium compound is $Pd(OAc)_2$ [palladium (II)acetate].

In some embodiments, the disclosure provides a process to manufacture a compound of formula VII:

VII

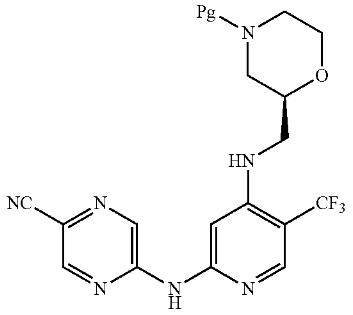

, the process comprising:

coupling a compound of formula V:

V

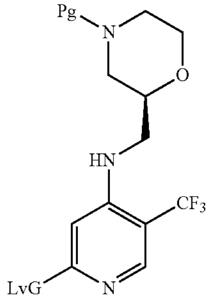

, with a compound of formula VI:

VI

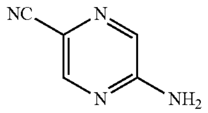

under cross coupling reaction conditions to form the compound of formula VII;

crystallizing and isolating the compound of formula VII from the reaction mixture;

wherein Pg is an organic group that is an amino protecting group and LvG is an organic group that is a leaving group.

In some embodiments, the process to manufacture the compound of formula VII further comprises:

a) providing a first mixture comprising the compound of formula V, the compound of formula VI, a catalyst, a ligand, and DMF;
b) providing a second mixture comprising an inorganic base and DMF, wherein the second mixture has been heated to between about 125-135° C.;
c) contacting the first mixture with the second mixture to provide a third mixture, wherein the temperature of the third mixture is maintained between about 125-135° C. for a period of time sufficient to produce the compound of formula VII.

In some embodiments, a process is provided to manufacture the compound of formula VII wherein N-Pg forms a sulfonamide group. In some embodiments, N-Pg forms a carbamate group. In some embodiments, N-Pg forms an amide group. In some embodiments, N-Pg forms a urea group.

In some embodiments, a process is provided to manufacture the compound of formula VII wherein Pg is selected form the group consisting of: Boc, Fmoc, acetamide, trifluoroacetamide, tosylate, mesylate, and allyl.

In some embodiments, isolating a compound is achieved by crystallization of the compound.

In some embodiments, the process of manufacturing the compound of formula VII comprises heating the mixture during the deprotection.

In some embodiments, the process of manufacturing the compound of formula VII comprises maintaining the temperature of the mixture at about 0° C., about 5° C., about 10° C., about 20° C., about 30° C., about 40° C., about 50° C., about 60° C., about 70° C. or about 80° C. during the deprotection step.

In some embodiments, the process of manufacturing the compound of formula VII comprises heating and no additional reagents to perform the deprotection.

In some embodiments, the process of manufacturing the compound of formula VII comprises heating the mixture during coupling.

In some embodiments, the process of manufacturing the compound of formula VII comprises cooling the mixture during crystallization.

In some embodiments, a process is provided to manufacture the compound of formula VII wherein the process further comprises maintaining the temperature of the mixture at about −78° C., about −15° C., about 0° C., about 10° C., about 20° C., about 30° C., about 40° C., or about 50° C. during crystallization.

III. Manufacture of SRA737

In another aspect, the present disclosure provides a process of manufacturing the compound of SRA737 according to formula VIII:

VIII

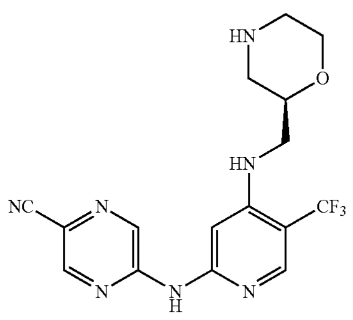

, the process comprising:

a) coupling the compound of formula XI:

XI

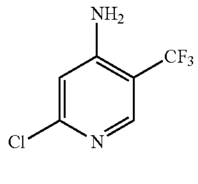

with the compound of formula II:

II

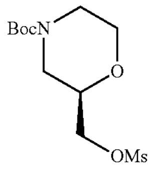

to provide the compound of formula XII:

XII

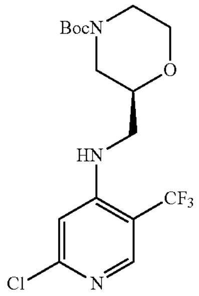

;

b) coupling the compound of formula XII:

XII

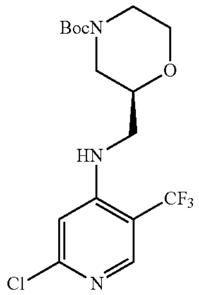

with the compound of formula VI:

VI

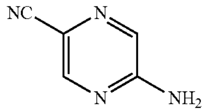

under cross coupling reaction conditions to provide the compound of formula X:

X

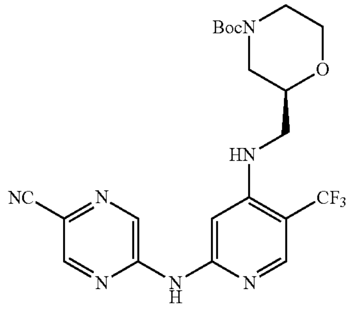

;

c) crystallizing and isolating the compound of formula X from the reaction mixture;

d) subjecting the compound of formula X to deprotection conditions to provide the compound of formula VIII.

In some embodiments, the process of manufacturing the compound of formula VIII further comprises:

a) providing a first mixture comprising the compound of formula XII, the compound of formula VI, a catalyst, a ligand, and DMF;

b) providing a second mixture comprising an inorganic base and DMF, wherein the second mixture has been heated to between about 125-135° C.;

c) contacting the first mixture with the second mixture to provide a third mixture, wherein the temperature of the third mixture is maintained between about 125-135° C. for a period of time sufficient to produce the compound of formula X.

In some embodiments, the process of manufacturing the compound of formula VIII comprises heating one or more of the mixtures for a period of time sufficient to produce the desired compound.

In some embodiments, the process of manufacturing the compound of formula VIII comprises heating the mixture during the deprotection.

In some embodiments, the process of manufacturing the compound of formula VIII comprises maintaining the temperature of the mixture at about 0° C., about 5° C., about 10° C., about 20° C., about 30° C., about 40° C., about 50° C., about 60° C., about 70° C. or about 80° C. during the deprotection step.

In some embodiments, the process of manufacturing the compound of formula VIII comprises heating and no additional reagents to perform the deprotection.

In some embodiments, the process of manufacturing the compound of formula VIII comprises heating the mixture during coupling.

In some embodiments, the process of manufacturing the compound of formula VIII comprises cooling the mixture during crystallization.

In some embodiments, a process is provided to manufacture the compound of formula VIII wherein the process further comprises maintaining the temperature of the mixture at about −78° C., about −15° C., about 0° C., about 10° C., about 20° C., about 30° C., about 40° C., or about 50° C. during crystallization.

In another aspect, the disclosure provides a process of manufacturing the compound salt of formula IX:

IX

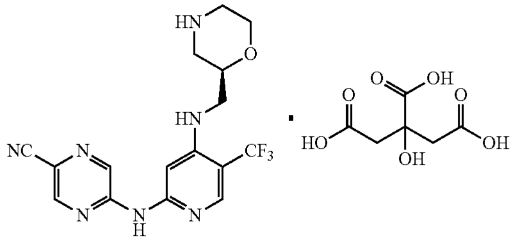

, the process comprising:

a) providing a first mixture comprising the compound of formula VIII:

VIII

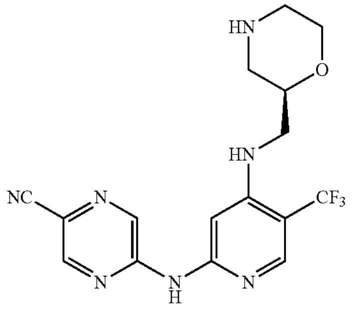

, acetic acid, water and an alcohol;

b) combining the first mixture with citric acid to provide a second mixture;

c) crystallizing and isolating the compound salt of formula IX:

IX

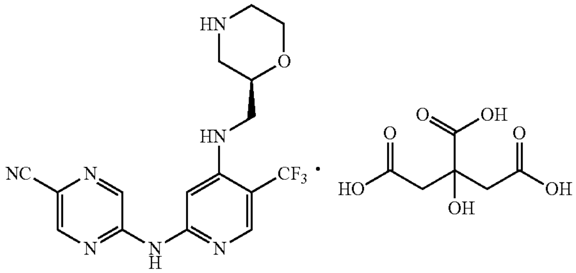

from the second mixture.

In some embodiments, the first mixture is prepared by combining the compound of formula VIII, acetic acid, water, and an alcohol at about 30-45° C.

In some embodiments, the second mixture is prepared by combining the first mixture with citric acid at about 20-25° C.

In some embodiments, the alcohol is selected from a group consisting of methanol, ethanol, propanol, butanol, pentanol, tert-butanol, and isopropanol.

IV. Crystallizing Solvates

In another aspect, the disclosure provides a process for preparing the solvate of any one of the compounds disclosed herein, the process comprising crystallizing the solvate from a mixture comprising a compound, water, and dimethylformamide (DMF).

In some embodiments, the disclosure provides a process for preparing the solvate of any one of the compounds disclosed herein, wherein the process further comprises maintaining the temperature of the mixture at about −78° C., about −15° C., about 0° C., about 10° C., about 20° C., about 30° C., about 40° C., or about 50° C. during crystallization.

In one some embodiments, the disclosure provides a process for preparing the solvate of a compound of formula VII:

VII

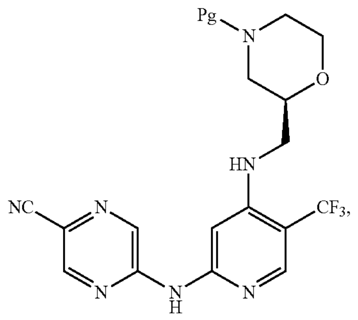

the process comprising crystallizing the solvate from a mixture comprising the compound of formula VII, water, and dimethylformamide (DMF).

In some embodiments, the disclosure provides a process for preparing the solvate of a compound of formula VII, the process comprising crystallizing the solvate from a mixture comprising a compound of formula VII, water, and dimethylformamide (DMF), wherein Pg is selected form the group consisting of Boc, Fmoc, acetamide, trifluoroacetamide, tosylate, mesylate, and allyl.

Compounds

The present disclosure provides compounds that are novel synthetic intermediates in the total synthesis process of SRA737.

In yet another aspect, the present disclosure provides novel solvates and crystalline solids of heterocyclic compounds described herein.

In some embodiments, the present disclosure provides a novel solvate of a protected form of SRA737 comprising a nitrogen atom protecting group (Pg).

In some embodiments, the compound is a solvate form of a compound of formula I:

I

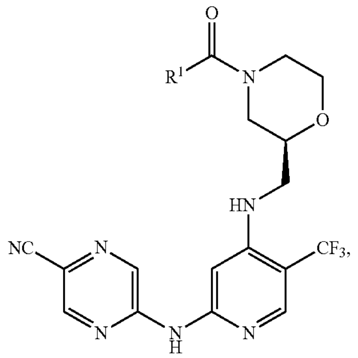

wherein $R^1$ is selected from the group consisting of $C_{1-12}$ alkyl, substituted $C_{1-12}$ alkyl, $C_{1-12}$ alkenyl, substituted $C_{1-12}$ alkenyl, $C_{1-12}$ alkynyl, substituted $C_{1-12}$ alkynyl, $C_{1-12}$ alkoxy, substituted $C_{1-12}$ alkoxy, $C_{3-8}$ cycloalkyl, substituted $C_{3-8}$ cycloalkyl, $C_{3-8}$ heterocycloalkyl, substituted $C_{3-8}$ heterocycloalkyl, $C_{1-12}$ amino, $C_{1-12}$ substituted amino, phenyl, substituted phenyl, $C_{3-8}$ heteroaryl, and substituted $C_{3-8}$ heteroaryl;

and wherein the solvate is a dimethylformamide (DMF) solvate.

In some embodiments, the compound is a solvate form of a compound of formula I wherein R1 is C1-12 alkoxy or substituted C1-12 alkoxy.

In some embodiments, the compound is a solvate form of a compound of formula I wherein R1 is substituted C12 alkoxy.

In some embodiments, the compound is a solvate form of a compound of formula I wherein R1 is C1-12 alkyl or substituted C1-12 alkyl.

In some embodiments, the compound is a solvate form of a compound of formula I wherein R1 is C1 alkyl.

In some embodiments, the compound is a solvate form of a compound of formula I wherein R1 is substituted C1 alkyl.

In some embodiments, the compound is a solvate form of a compound of formula I wherein R1 is substituted C10 alkyl.

In some embodiments, the compound is a solvate form of a compound of formula I wherein R1 is substituted C12 alkyl.

In some embodiments, the compound is a solvate form of a compound of formula I wherein R1 is C10 alkyl.

In some embodiments, the compound is a solvate form of a compound of formula I wherein R1 is substituted C2 alkyl.

In some embodiments, the compound is a solvate form of a compound of formula I wherein R1 is C2 alkyl.

In some embodiments, the compound is a solvate form of a compound of formula I wherein R1 is C3-8 cycloalkyl or substituted C3-8 cycloalkyl.

In some embodiments, the compound is a solvate form of a compound of formula I wherein R1 is C3 cycloalkyl.

In some embodiments, the compound is a solvate form of a compound of formula I wherein R1 is C5 cycloalkyl.

In some embodiments, the compound is a solvate form of a compound of formula I wherein R1 is C6 cycloalkyl.

In some embodiments, the compound is a solvate form of a compound of formula I wherein R1 is C3-8 heterocycloalkyl or C3-8 heteroaryl.

In some embodiments, the compound is a solvate form of a compound of formula I wherein R1 is C3 heterocycloalkyl.

In some embodiments, the compound is a solvate form of a compound of formula I wherein R1 is C4 heterocycloalkyl.

In some embodiments, the compound is a solvate form of a compound of formula I wherein R1 is C5 heterocycloalkyl, wherein the C5 heterocycloalkyl contain 1 nitrogen atom.

In some embodiments, the compound is a solvate form of a compound of formula I wherein R1 is C6 heterocycloalkyl, wherein the C6 heterocycloalkyl contain 1 nitrogen atom.

In some embodiments, the compound is a solvate form of a compound of formula I wherein R1 is C1-12 alkenyl or substituted C1-12 alkenyl.

In some embodiments, the compound is a solvate form of a compound of formula I wherein R1 is C2 alkenyl.

In some embodiments, the compound is a solvate form of a compound of formula I wherein R1 is C3 alkenyl.

In some embodiments, the compound is a solvate form of a compound of formula I wherein R1 is substituted C2 alkenyl.

In some embodiments, the compound is a solvate form of a compound of formula I wherein R1 is —OC(CH3)3.

In some embodiments, the compound is a solvate form of a compound of formula I wherein R1 is —C(CH3)3.

In some embodiments, the compound is a solvate form of a compound of formula I wherein R1 is —CH(CH3)2.

In some embodiments, the compound is a solvate form of a compound of formula I wherein R1 is —O(CH)CH2.

In some embodiments, the compound is a solvate form of a compound of formula I wherein R1 is —OCH2(CH)CH2.

In some embodiments, the compound is a solvate of any one of compounds disclosed herein and which is substantially purified.

In some embodiments, the compound is a solvate of any one of compounds disclosed herein and which is substantially free of small molecule impurities.

In some embodiments, the compound is a solvate of any one of compounds disclosed herein and which is substantially purified in that is free of small organic compounds (<500 Da) that are impurities carried forward, i.e. organic compounds that are side products from the reaction to make the intermediate, SRA737, protected form of SRA737, compound of Formula I, or any other compound disclosed herein.

In some embodiments, the compound is a solvate form of any one of the compounds disclosed herein and is substantially free of impurities, i.e. a small molecule that is an undesired isomer of the disclosed compounds.

In some embodiments, the compound is purified by crystallization. In a further embodiment, the compound is further purified by recrystallization from a polar aprotic solvent.

In some embodiments, the recrystallization process comprises:

a) mixing the purified crystalline form of a compound disclosed herein with a polar aprotic solvent;
b) heating the mixture to a temperature of about 30° C., about 40° C., about 50° C., about 60° C., about 70° C., about 80° C., about 90° C., about 100° C., or about 110° C.;
c) cooling the mixture to a temperature of about 40° C., about 30° C., about 20° C., about 10° C., about 0° C., about −10° C., about −20° C., about −30° C., or about −78° C.;
d) isolating the recrystallized crystalline form of the compound.

In some embodiments, the polar aprotic solvent comprises acetonitrile, dimethylformamide, ethanol, methanol, isopropanol, tetrahydrofuran, pyridine and diethyl ether.

In some embodiments, the compound is a solvate of any one of the compounds disclosed herein and which is substantially purified or is substantially free of impurities. In some embodiments, the compound is a solvate of any one of the compounds disclosed herein and which is substantially purified or is substantially free of impurities and is crystalline. In some embodiments, the compound is a solvate of any one of the compounds disclosed herein and which is substantially purified or is substantially free of palladium impurities. In some embodiments, the compound is a solvate of any one of the compounds disclosed herein and which is substantially purified or is substantially free of organic impurities. In some embodiments, the compound is a solvate of any one of the compounds disclosed herein and which is substantially purified or is substantially free of organic and palladium impurities. In some embodiments, the compound is crystalline and is a polymorph. In some embodiments, the compound is polymorphic and has more than one form.

I. Synthetic Intermediates

In some embodiments, the compound is a solid form of a compound of formula VII:

VII

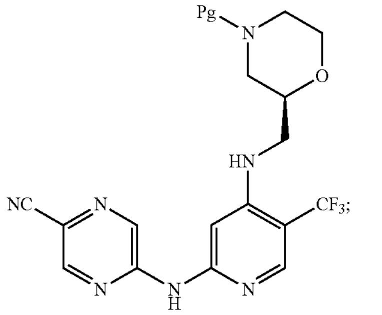

wherein Pg is an organic group that is an amino protecting group.

In some embodiments, the compound of formula VII is a crystalline compound. In some embodiments, the compound of formula VII is a semi-crystalline compound. In some embodiments, the compound of formula VII is an amorphous compound. In some embodiments, the compound of formula VII is a solid form of compound having one or more polymorphic forms.

In some embodiments, the compound of formula VII has a Pg group that is selected from the group consisting of: acyl, formyl, acylamino, aminocarbonyl, aminothiocarbonyl, aminosulfonyl, amidino, carboxy ester, benzyl, benzyidene, hydroxy, substituted sulfonyl, substituted sulfinyl, and sulfonyloxy. In some embodiments, the compound of formula VII has a Pg group that is selected from the group consisting of: Boc, Ms, Ts, benzyl (—$CH_2$Ph), allyl

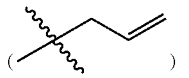 [SMILES: *CC=C]

and vinyl.

In some embodiments, the compound of formula VII has a Pg group that is Boc.

In some embodiments, the compound of formula VII has a Pg group that is allyl

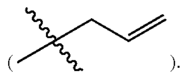

In some embodiments, the compound of formula VII has a Pg group that is Ts.

In some embodiments, the compound of formula VII has a Pg group that is Fmoc.

In some embodiments, the compound of formula VII has a Pg group that is trimethysilyl (TMS).

In some embodiments, the compound of formula VII has a Pg group that is vinyl.

In some embodiments, the compound of formula VII is a crystalline compound. In some embodiments, the compound of formula VII is a semi-crystalline compound. In some embodiments, the compound of formula VII is an amorphous compound. In some embodiments, the compound of formula VII is a solid form of compound having one or more polymorphic forms.

In some embodiments, the compound is a solid form of formula II, of formula VII, or of formula VIII. In some embodiments, the compound is a crystalline or semi-crystalline solid form of formula II.

In some embodiments, the compound is a crystalline solid form of the compound of formula II:

II

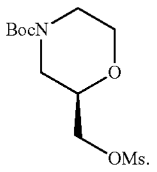

In some embodiments, the compound is a crystalline solid form of a compound of formula II: having an X-ray powder diffraction pattern comprising a peak, in terms of 2-theta, at about 12.9°, about 18.1°, about 20.6°, about 21.6°, about 22.3°, about 26.5°, and 27.8°.

Figure 2:
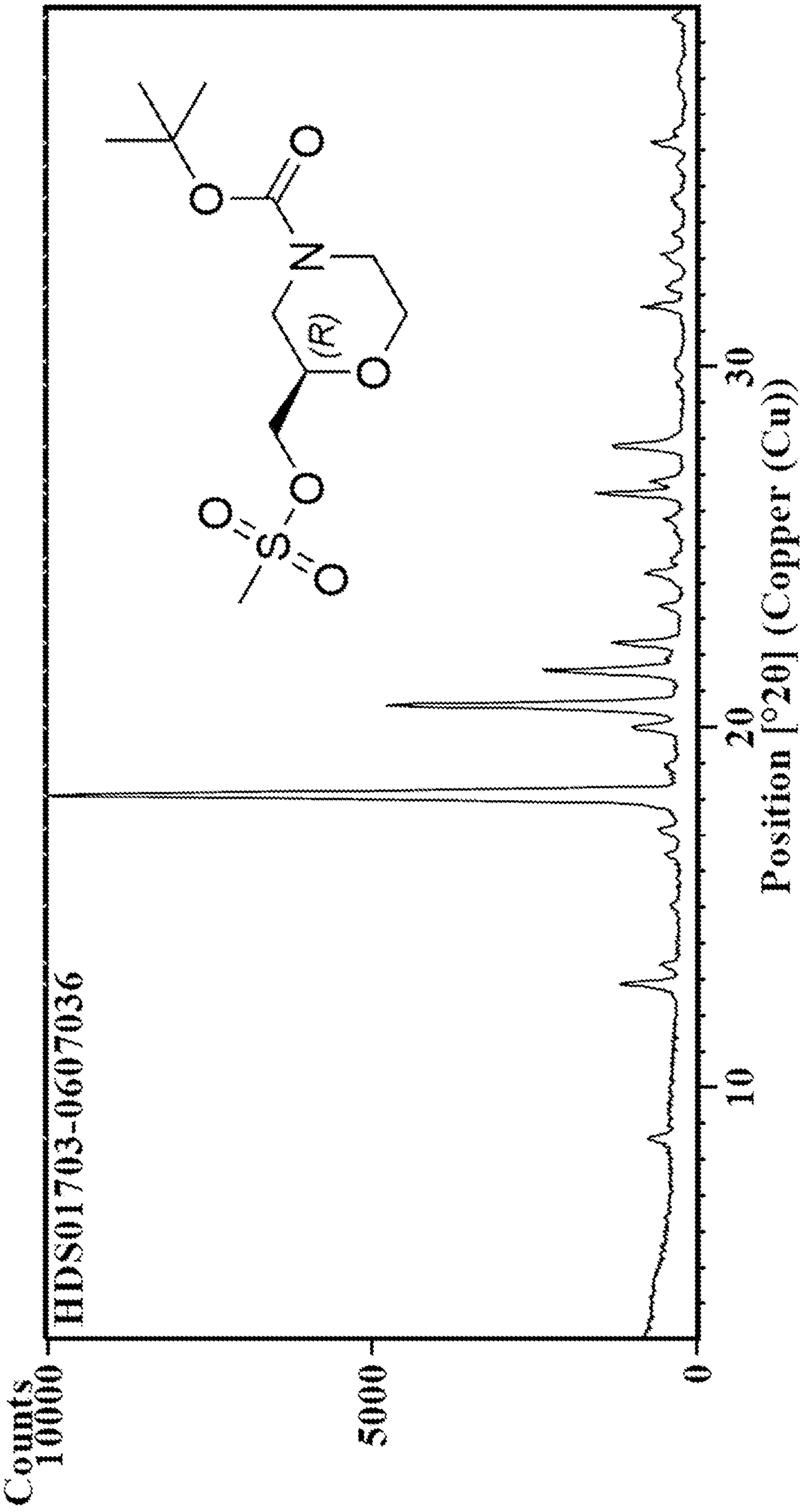
FIG. 2 shows the X-ray powder diffraction pattern (XRPD) of the crystalline solid form of the compound of formula II.

In some embodiments, the compound is a crystalline solid form of a compound of formula II: having an X-ray powder diffraction pattern substantially as shown in FIG. 2.

In some embodiments, the compound is a crystalline solid form of a compound of formula II: having a differential scanning calorimetry (DSC) thermogram comprising an endothermic peak at about 215.1° C.

Figure 3:
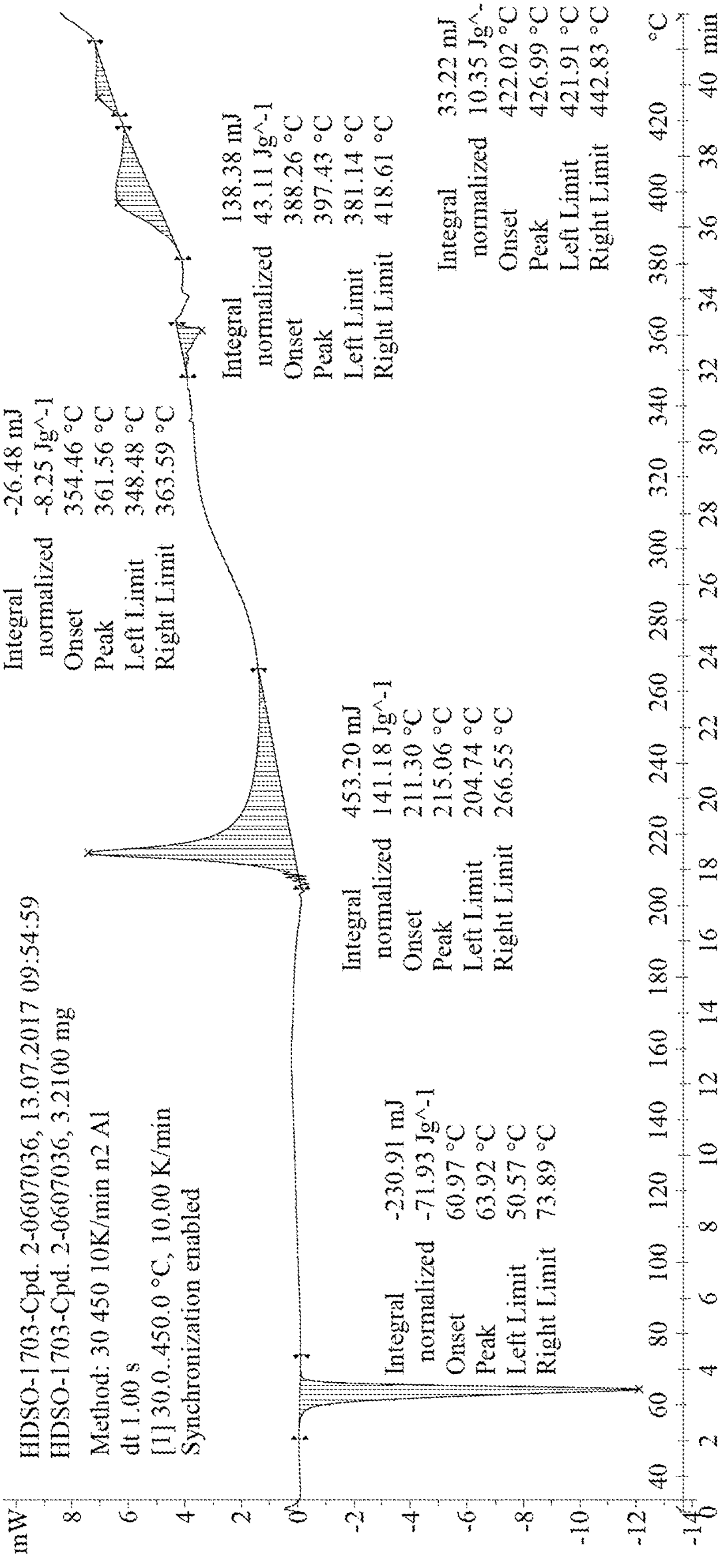
FIG. 3 shows the differential scanning calorimetry (DSC) thermogram of the crystalline solid form of the compound of formula II.

In some embodiments, the compound is a crystalline solid form of a compound of formula II: having a differential scanning calorimetry (DSC) thermogram substantially as shown in FIG. 3.

Figure 4:
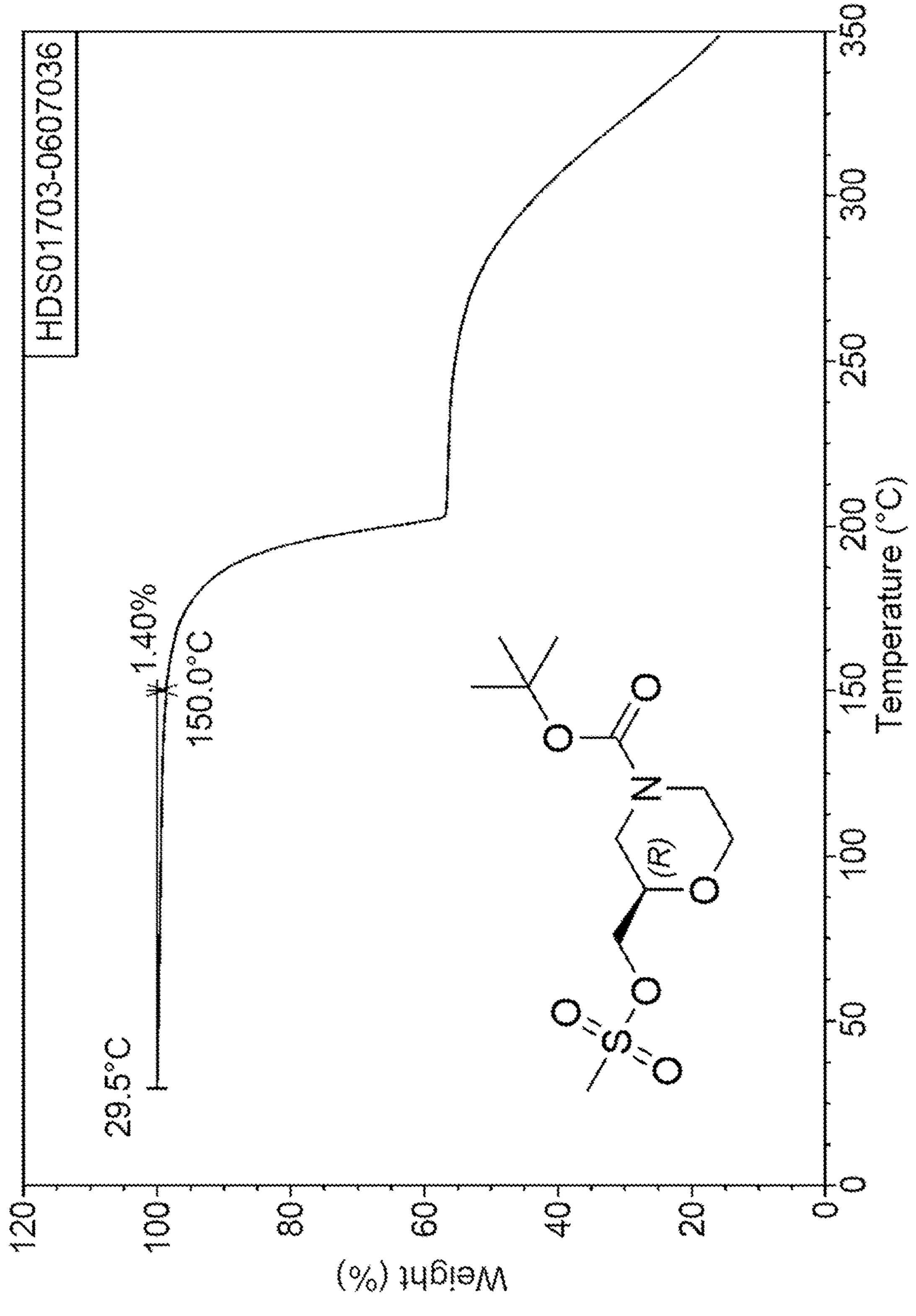
FIG. 4 shows the thermogravimetric analysis (TGA) of the crystalline solid form of the compound of formula II.

In some embodiments, the compound is a crystalline solid form of a compound of formula II: having a thermogravimetric analysis (TGA) substantially as shown in FIG. 4.

In some embodiments, the compound is a crystalline solid form of a compound of formula II: which is substantially purified or is substantially free of impurities. In some embodiments, the crystalline solid form of a compound of formula II is substantially free of organic compound impurities.

In some embodiments, the compound is a crystalline solid form of the compound of formula X:

X

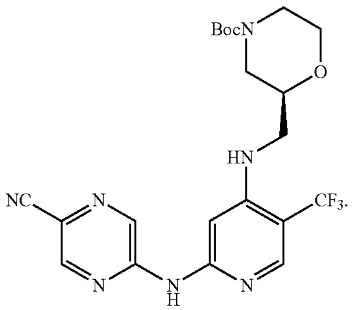

In some embodiments, the compound is a crystalline solid form of a compound of formula X: having an X-ray powder diffraction pattern comprising a peak, in terms of °2Th, at about 5.6°, about 11.1°, about 14.8°, about 16.7°, about 19.0°, about 19.4°, about 24.4°, and about 28.0°.

Figure 5:
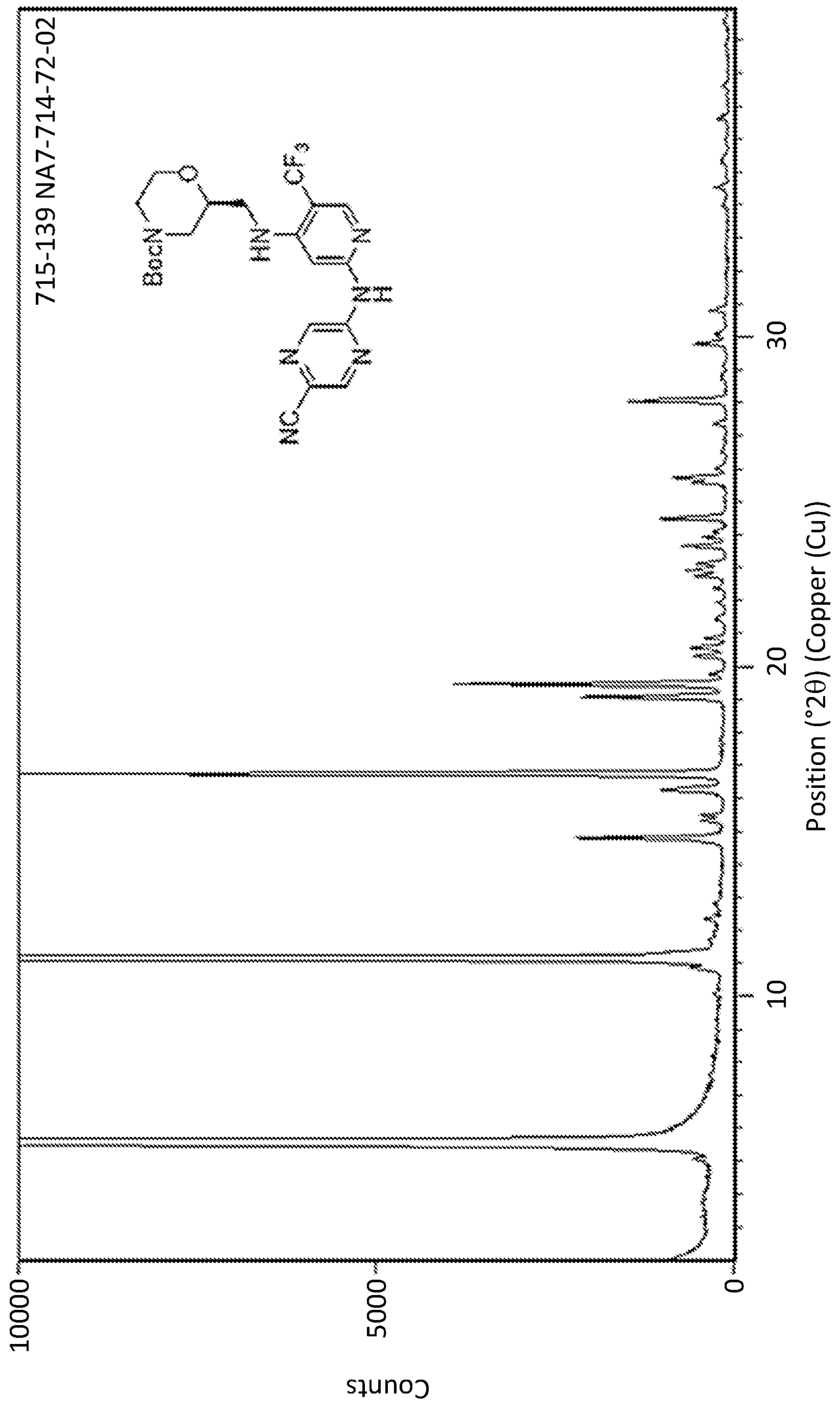
FIG. 5 shows the X-ray powder diffraction pattern (XRPD) of the crystalline solid form of a compound of formula X.
Figure 6:
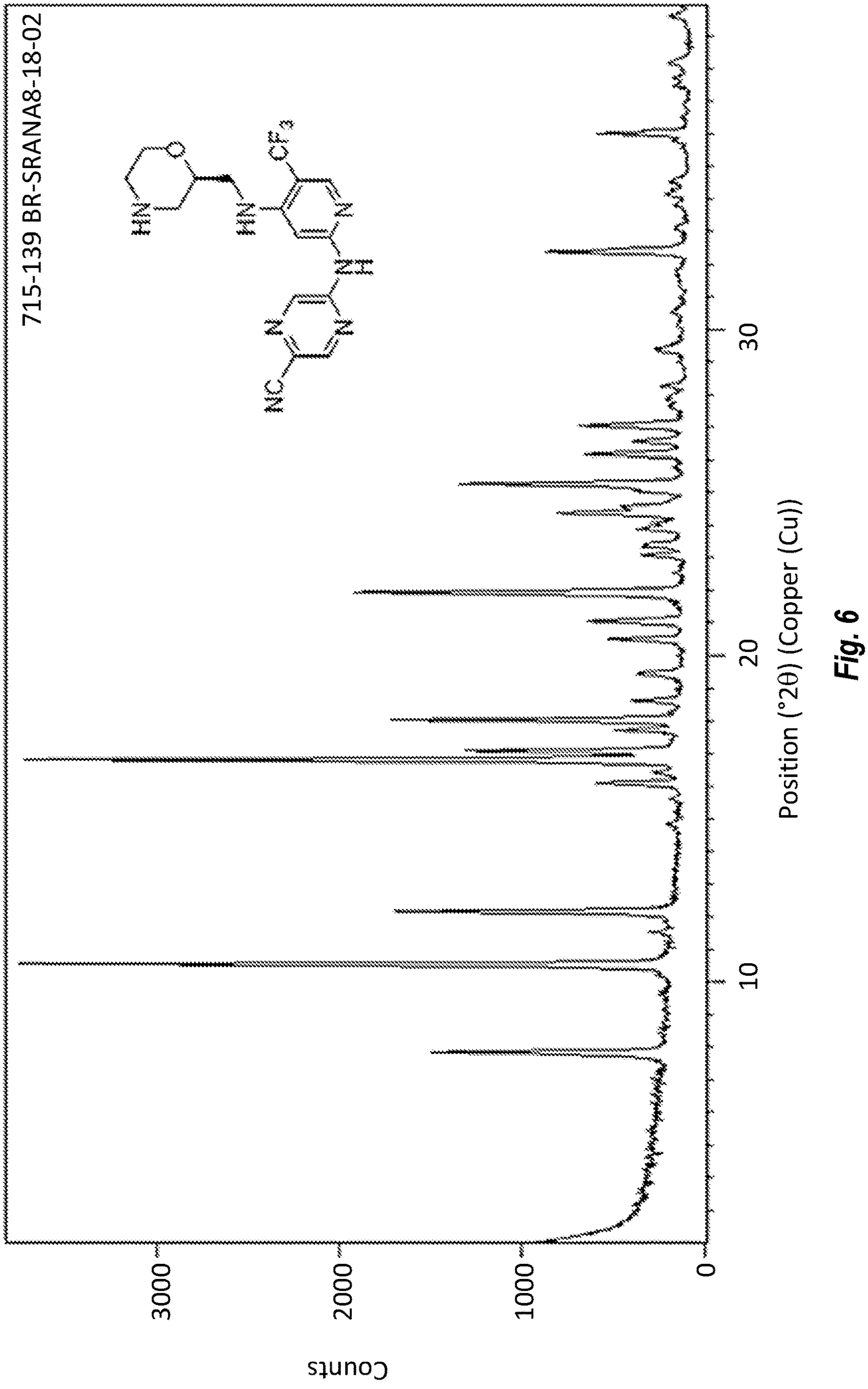
FIG. 6 shows the X-ray powder diffraction pattern (XRPD) of the crystalline solid form of a compound of formula VIII.

In some embodiments, the compound is a crystalline solid form of the compound of formula X: having an X-ray powder diffraction pattern substantially as shown in FIG. 5.

II. General Methods to Make and Use Solvates and Synthetic Intermediates

The solvate and/or solid form compounds described herein can be prepared from readily available starting materials using the following general methods and procedures.

Briefly, a morpholine derivative (formula I or another such derivative compound possessing for instance, a differing nitrogen protecting group than Boc or a differing handle group than hydroxy) is transformed into a mesylated compound that may be crystalline. This mesylated morpholine intermediate product can then undergo nucleophilic displacement by an amino-pyridine heterocyclic compound (optionally substituted), optionally in the presence of a weak inorganic or organic base. The resulting intermediate product is then optionally purified on a silica-gel packed chromatography column or by filtration and washing or by crystallization.

The purified intermediate product can then be coupled with an amino-pyrazine compound, optionally substituted. The resulting intermediate product is precipitated out and then carried forward to be de-protected on the nitrogen atom to give the desired final product.

The starting materials for the following reactions are generally known compounds or can be prepared by known procedures or obvious modifications thereof. For example, many of the starting materials are available from commercial suppliers such as Aldrich Chemical Co. (Milwaukee, Wisconsin, USA), Bachem (Torrance, California, USA), Emka-Chemce or Sigma (St. Louis, Missouri, USA), CombiChem (San Diego, CA). Others may be prepared by procedures, or obvious modifications thereof, described in standard reference texts such as Fieser and Fieser's Reagents for Organic Synthesis, Volumes 1-15 (John Wiley, and Sons, 1991), Rodd's Chemistry of Carbon Compounds, Volumes 1-5, and Supplementals (Elsevier Science Publishers, 1989), Organic Reactions, Volumes 1-40 (John Wiley, and Sons, 1991), March's Advanced Organic Chemistry, (John Wiley, and Sons, 5th Edition, 2001), and Larock's Comprehensive Organic Transformations (VCH Publishers Inc., 1989).

It will also be appreciated that where typical process conditions (i.e., reaction temperatures, times, mole ratios of reactants, solvents, pressures, etc.) are given to make these compounds, minor modifications to these process conditions can also be used unless otherwise stated. Optimum reaction conditions may vary with the particular reactant or solvent used, but such conditions can be determined by one skilled in the art by routine optimization procedures as long as the reagents stay the same.

Additionally, as will be apparent to those skilled in the art, conventional protecting groups may be necessary to prevent certain functional groups from undergoing undesired reactions. Herein it is understood that amino, keto, thio, hydroxyl, and any other necessary protecting groups and their methods of deprotection are known in the art, such as those described in T. W. Greene and P. G. M. Wuts, Protecting Groups in Organic Synthesis, Third Edition, Wiley, New York, 1999, which is incorporated in its entirety along with the references cited therein.

If the compounds described herein contain one or more chiral centers, such compounds can be prepared or isolated as pure stereoisomers, i.e., as individual enantiomers or d(l) stereoisomers, or as stereoisomer-enriched mixtures. All such stereoisomers (and enriched mixtures) are included within the scope of the present technology, unless otherwise indicated. Pure stereoisomers (or enriched mixtures) may be prepared using, for example, optically active starting materials or stereoselective reagents well known in the art.

Alternatively, racemic mixtures of such compounds can be separated using, for example, chiral column chromatography, chiral resolving agents and the like.

Compositions

In another aspect, compositions are provided that comprise at least one compound as described herein. In some embodiments, compositions are provided that comprise at least one compound as described herein and an excipient and/or antioxidant and no more than about 1 ppm palladium impurity. In some embodiments, compositions are provided that comprise at least one compound as described herein and an excipient and/or antioxidant and no more than about 10 ppb, no more than about 5 ppb, no more than about 2 ppb, or no more than about 1 ppb palladium impurity. In some embodiments, compositions are provided that are at least about 99%, at least about 99.5%, at least about 99.7%, at least about 99.9%, or at least about 99.99% of the pure compound by weight. In some embodiments, the composition provided comprise one compound as described herein and an excipient and/or antioxidant. The skilled artisan will appreciate that these percentages for purity are each based on the relative amount of the desired compound in the dry weight composition.

I. Salt Form of SRA737

In another aspect, the present disclosure provides for a process of manufacturing salt forms of SRA737 (e.g., as described herein). In certain cases, the salt is a SRA737 citrate salt. In some instances, the SRA737 citrate salt comprises SRA737 with citric acid in a 1:1 ratio.

In some embodiments, the salt form of SRA737 is the compound salt of formula IX:

IX

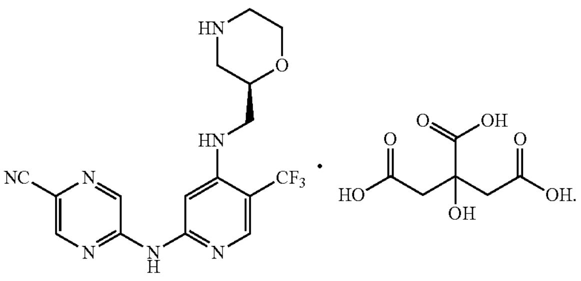

It is understood that the structure of formula IX is one representation of the salt form of SRA737 and that alternative representations are possible. All such representations of the salt are meant to be included.

In some embodiments, the process of manufacturing the compound salt of formula IX involves a process of crystallization.

In some embodiments, the compound is a crystalline solid form of a compound salt of formula IX.

In some embodiments, the compound is a crystalline solid form of a compound salt of formula IX having an X-ray powder diffraction pattern comprising a peak, in terms of 2-theta, at about 5.9°, about 11.3° about 11.8°, about 14.5°, about 14.8°, about 17.8°, about 18.4° about 18.7° about 19.0° about 19.3° about 20.2° about 20.6° about 20.9° about 21.2° about 21.7° about 23.0° about 23.7° about 24.0° about 24.4° and about 24.7°.

Figure 7:
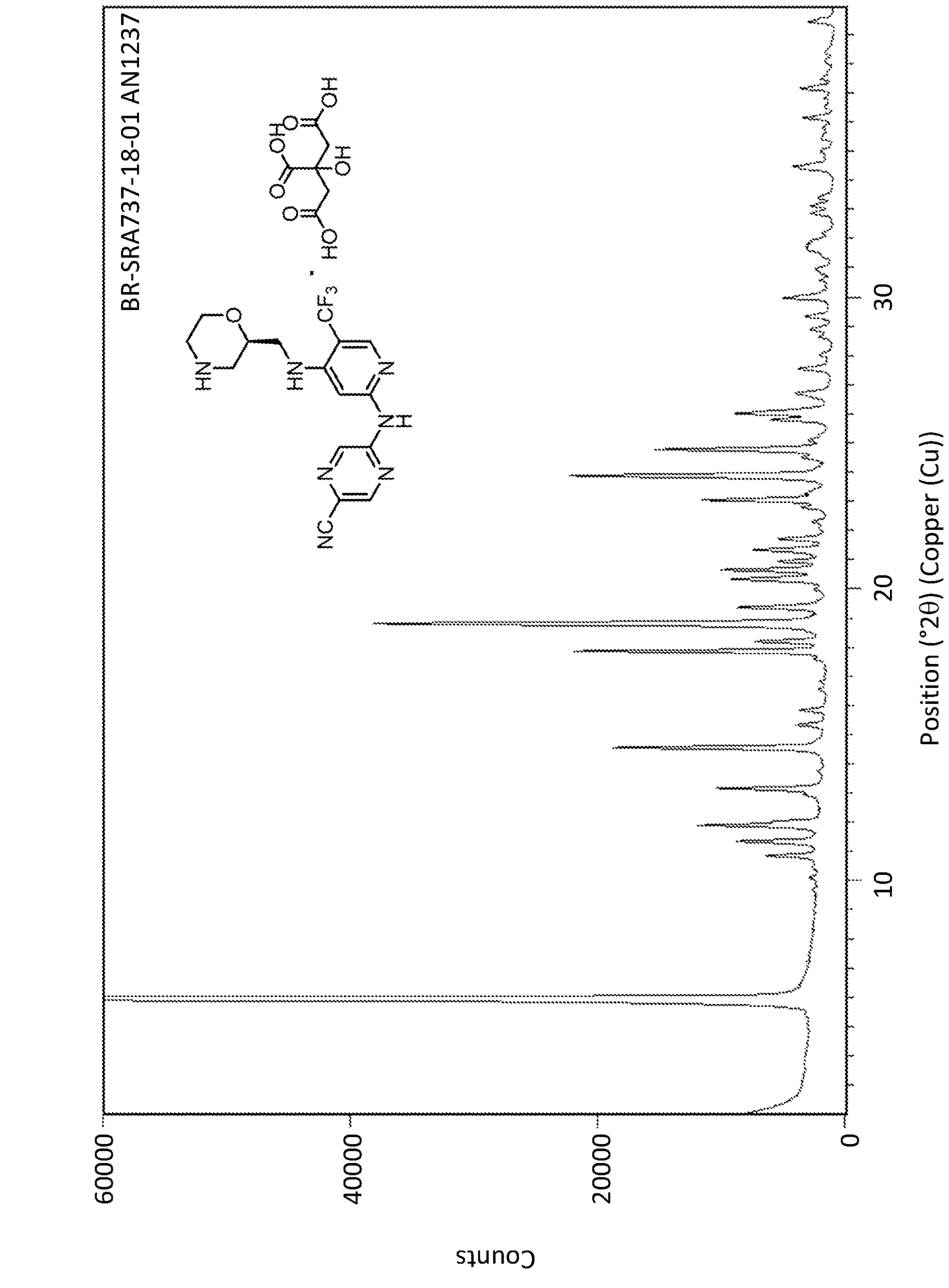
FIG. 7 shows the X-ray powder diffraction pattern (XRPD) of the crystalline solid form of the compound salt of formula IX.
Figure 8:
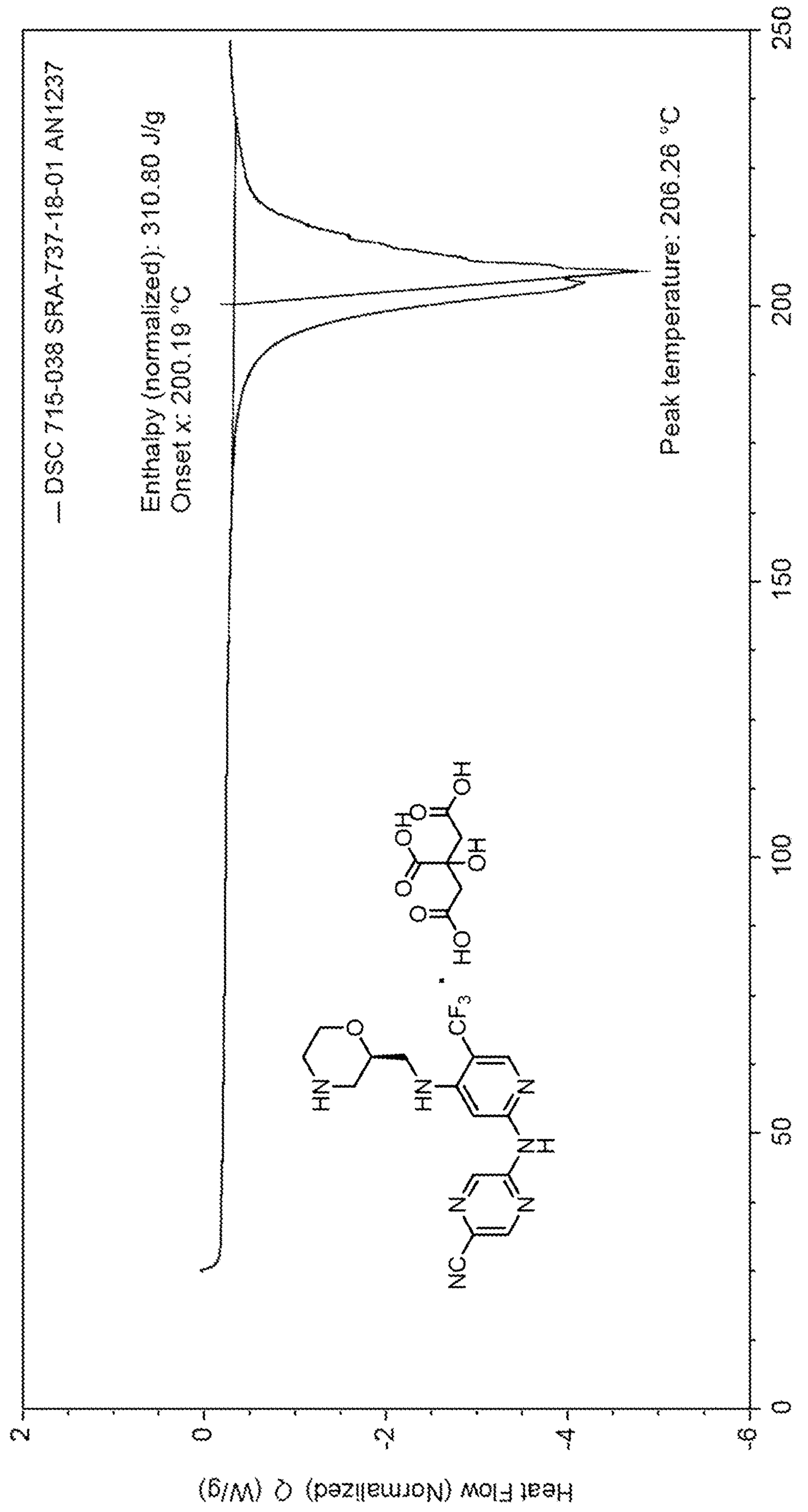
FIG. 8 shows the differential scanning calorimetry (DSC) thermogram of the crystalline solid form of compound salt of formula IX.

In some embodiments, the compound is a crystalline solid form of a compound salt of formula IX: having an X-ray powder diffraction pattern substantially as shown in FIG. 7.

II. Pharmaceutical Compositions

In a further aspect, pharmaceutical compositions are provided that comprise SRA737 and very low concentrations of one or more palladium compounds as impurities as described herein and a pharmaceutically acceptable carrier or excipient.

In some embodiments, the pharmaceutical composition comprises no more than 1 mol %, 0.9 mol %, 0.8 mol %, 0.7 mol %, 0.6 mol %, 0.5 mol %, 0.4 mol %, 0.3 mol %, 0.2 mol %, 0.1 mol %, 0.05 mol %, 0.04 mol %, 0.03 mol %, 0.02 mol %, 0.01 mol %, 0.005 mol %, 0.004 mol %, 0.003 mol %, 0.002 mol %, 0.001 mol % or 0.0001 mol % of one or more palladium compounds as impurities.

In some embodiments, the pharmaceutical composition comprises no more than 5 ppm, 4 ppm, 3 ppm, 2 ppm, 1 ppm, 0.9 ppm, 0.8 ppm, 0.7 ppm, 0.6, ppm, 0.5 ppm, 0.4 ppm, 0.3 ppm, 0.2 ppm, 0.1 ppm, 0.05 ppm. 0.04 ppm, 0.03 ppm, 0.02 ppm or 0.01 ppm of one or more palladium compounds as impurities.

In some embodiments, the pharmaceutical compositions comprise no more than 5 ng/ml, 4 ng/ml, 3 ng/ml, 2 ng/ml, 1 ng/ml, 0.9 ng/ml, 0.8 ng/ml, 0.7 ng/ml, 0.6 ng/ml, 0.5 ng/ml, 0.4 ng/ml, 0.3 ng/ml, 0.2 ng/ml, 0.1 ng/ml, 0.09 ng/ml, 0.08 ng/ml, 0.07 ng/ml, 0.06 ng/ml, 0.05 ng/ml, 0.04 ng/ml, 0.03 ng/ml, 0.02 ng/ml, 0.01 ng/ml, 0.005 ng/ml, 0.004 ng/ml, 0.003 ng/ml, 0.002 ng/ml or 0.001 ng/ml of one or more palladium compounds as impurities.

In some embodiments, the pharmaceutical compositions comprise no less than 100:1, 200:1, 300:1, 400:1, 500:1, 600:1, 700:1, 800:1, 900:1, 1000:1, 2000:1, 3000:1, 4000:1, 5000:1, 6000:1, 7000:1, 8000:1, 9000:1, 10,000:1, 50,000:1 or 100,000:1 weight ratios of SRA737 to one or more palladium compounds as impurities.

In some embodiments, the pharmaceutical compositions comprise 100:1, 200:1, 300:1, 400:1, 500:1, 600:1, 700:1, 800:1, 900:1, 1000:1, 2000:1, 3000:1, 4000:1, 5000:1, 6000:1, 7000:1, 8000:1, 9000:1, 10,000:1, 50,000:1 or 100,000:1 weight ratios of SRA737 salt form, measured as free base of SRA737, to one or more palladium compounds as impurities.

In some embodiments, the pharmaceutical compositions comprise SRA737 and very low concentrations of one or more organic compounds as impurities as described herein.

In some embodiments, the pharmaceutical composition comprises no more than 1 mol %, 0.9 mol %, 0.8 mol %, 0.7 mol %, 0.6 mol %, 0.5 mol %, 0.4 mol %, 0.3 mol %, 0.2 mol %, 0.1 mol %, 0.05 mol %, 0.04 mol %, 0.03 mol %, 0.02 mol %, 0.01 mol %, 0.005 mol %, 0.004 mol %, 0.003 mol %, 0.002 mol %, 0.001 mol % or 0.0001 mol % of one or more organic compounds as impurities.

In some embodiments, the pharmaceutical composition comprises no more than 5 ppm, 4 ppm, 3 ppm, 2 ppm, 1 ppm, 0.9 ppm, 0.8 ppm, 0.7 ppm, 0.6, ppm, 0.5 ppm, 0.4 ppm, 0.3 ppm, 0.2 ppm, 0.1 ppm, 0.05 ppm. 0.04 ppm, 0.03 ppm, 0.02 ppm or 0.01 ppm of one or more organic compounds as impurities.

In some embodiments, the pharmaceutical compositions comprise no more than 5 ng/ml, 4 ng/ml, 3 ng/ml, 2 ng/ml, 1 ng/ml, 0.9 ng/ml, 0.8 ng/ml, 0.7 ng/ml, 0.6 ng/ml, 0.5 ng/ml, 0.4 ng/ml, 0.3 ng/ml, 0.2 ng/ml, 0.1 ng/ml, 0.09 ng/ml, 0.08 ng/ml, 0.07 ng/ml, 0.06 ng/ml, 0.05 ng/ml, 0.04 ng/ml, 0.03 ng/ml, 0.02 ng/ml, 0.01 ng/ml, 0.005 ng/ml, 0.004 ng/ml, 0.003 ng/ml, 0.002 ng/ml or 0.001 ng/ml of one or more organic compounds as impurities.

In some embodiments, the pharmaceutical compositions comprise no less than 100:1, 200:1, 300:1, 400:1, 500:1, 600:1, 700:1, 800:1, 900:1, 1000:1, 2000:1, 3000:1, 4000:1, 5000:1, 6000:1, 7000:1, 8000:1, 9000:1, 10,000:1, 50,000:1 or 100,000:1 weight ratios of SRA737 to one or more organic compounds as impurities.

In some embodiments, the pharmaceutical compositions comprise 100:1, 200:1, 300:1, 400:1, 500:1, 600:1, 700:1, 800:1, 900:1, 1000:1, 2000:1, 3000:1, 4000:1, 5000:1, 6000:1, 7000:1, 8000:1, 9000:1, 10,000:1, 50,000:1 or 100,000:1 weight ratios of SRA737 salt form, measured as free base of SRA737, to one or more organic compounds as impurities.

In some embodiments, the pharmaceutical compositions comprise SRA737 and very low concentrations of one or more palladium compounds and one or more organic compounds all together as impurities as described herein.

In some embodiments, the pharmaceutical composition comprises no more than 1 mol %, 0.9 mol %, 0.8 mol %, 0.7 mol %, 0.6 mol %, 0.5 mol %, 0.4 mol %, 0.3 mol %, 0.2 mol %, 0.1 mol %, 0.05 mol %, 0.04 mol %, 0.03 mol %, 0.02 mol %, 0.01 mol %, 0.005 mol %, 0.004 mol %, 0.003 mol %, 0.002 mol %, 0.001 mol % or 0.0001 mol % of one or more palladium compounds and one or more organic compounds all together as impurities.

In some embodiments, the pharmaceutical composition comprises no more than 5 ppm, 4 ppm, 3 ppm, 2 ppm, 1 ppm, 0.9 ppm, 0.8 ppm, 0.7 ppm, 0.6, ppm, 0.5 ppm, 0.4 ppm, 0.3 ppm, 0.2 ppm, 0.1 ppm, 0.05 ppm. 0.04 ppm, 0.03 ppm, 0.02 ppm or 0.01 ppm of one or more palladium compounds and one or more organic compounds all together as impurities.

In some embodiments, the pharmaceutical compositions comprise no more than 5 ng/ml, 4 ng/ml, 3 ng/ml, 2 ng/ml, 1 ng/ml, 0.9 ng/ml, 0.8 ng/ml, 0.7 ng/ml, 0.6 ng/ml, 0.5 ng/ml, 0.4 ng/ml, 0.3 ng/ml, 0.2 ng/ml, 0.1 ng/ml, 0.09 ng/ml, 0.08 ng/ml, 0.07 ng/ml, 0.06 ng/ml, 0.05 ng/ml, 0.04 ng/ml, 0.03 ng/ml, 0.02 ng/ml, 0.01 ng/ml, 0.005 ng/ml, 0.004 ng/ml, 0.003 ng/ml, 0.002 ng/ml or 0.001 ng/ml of one or more palladium compounds and one or more organic compounds all together as impurities.

In some embodiments, the pharmaceutical compositions comprise 100:1, 200:1, 300:1, 400:1, 500:1, 600:1, 700:1, 800:1, 900:1, 1000:1, 2000:1, 3000:1, 4000:1, 5000:1, 6000:1, 7000:1, 8000:1, 9000:1, 10,000:1, 50,000:1 or 100,000:1 weight ratios of SRA737 to one or more palladium compounds and one or more organic compounds all together as impurities.

In some embodiments, the pharmaceutical compositions comprise 100:1, 200:1, 300:1, 400:1, 500:1, 600:1, 700:1, 800:1, 900:1, 1000:1, 2000:1, 3000:1, 4000:1, 5000:1, 6000:1, 7000:1, 8000:1, 9000:1, 10,000:1, 50,000:1 or 100,000:1 weight ratios of SRA737 salt form, measured as free base of SRA737, to one or more palladium compounds and one or more organic compounds all together as impurities.

In some embodiments, the pharmaceutical compositions comprise 1, 2, 3, 4, or 5 or more of the herein described compounds, with SRA737 being the API and the other organic compounds, as trace impurities. In some embodiments, the composition comprises a plurality of compounds.

In some embodiments, the pharmaceutical composition comprises at least one compound of Formula I, or tautomers, stereoisomers, salts, solvates or hydrates thereof.

In some embodiments, the pharmaceutical composition comprises at least one compound of Formula II, or tautomers, stereoisomers, salts, solvates or hydrates thereof.

In some embodiments, the pharmaceutical composition is formulated for enteral route of administration. In various embodiments, the pharmaceutical composition is formulated for intravenous route of administration.

Pharmaceutical compositions for enteral route of administration can be in tablet, capsule, powder or liquid form. A tablet can include a solid carrier such as gelatin or an adjuvant. Liquid pharmaceutical compositions generally include a liquid carrier such as water, petroleum, animal or vegetable oils, mineral oil or synthetic oil. Physiological saline solution, dextrose or other saccharide solution or glycols such as ethylene glycol, propylene glycol or polyethylene glycol can be included. A pharmaceutical composition can include a cyclodextrin. A pharmaceutical composition can contain poloxamer and/or D-α-Tocopheryl polyethylene glycol 1000 succinate (Vitamin E TPGS).

In some embodiments in which the pharmaceutical composition is formulated for enteral route of administration in a solid dosage form, the composition will contain, on a weight percent (wt %) basis, from about 0.01-99.99 wt % of the compound of the present technology based on the total formulation, with the balance being one or more suitable pharmaceutical excipients. Preferably, the compound is present at a level of about 1-80 wt %.

In some embodiments, the pharmaceutical composition is formulated for inhalation suspended in solutions or mixtures of excipients (e.g., preservatives, viscosity modifiers, emulsifiers, buffering agents) in non-pressurized or pressurized dispensers that deliver a spray containing a metered dose of at least one compound as described herein. In certain inhalation embodiments, the pharmaceutical composition is formulated for nasal or oral administration.

In some embodiments, the pharmaceutical composition is formulated for topical administration. In certain topical embodiments, the pharmaceutical composition is formulated for enepidermic route, Epidermic route, Instillation administration, or Painting/Swabbing.

In some embodiments, the pharmaceutical composition is formulated for parenteral administration. In certain parenteral embodiments, the pharmaceutical composition is formulated for intravenous, subcutaneous, or intradermal administration. In some embodiments, the pharmaceutical composition is formulated for intrathecal or intracerebroventricular administration.

In typical parenteral embodiments, the composition will be in the form of a parenterally acceptable aqueous solution that is pyrogen-free and has suitable pH, isotonicity and stability. Those of relevant skill in the art are well able to prepare suitable solutions using, for example, isotonic vehicles such as Sodium Chloride Injection, Ringer's Injection, Lactated Ringer's Injection. Preservatives, stabilizers, buffers, antioxidants and/or other additives can be included, as required.

EXAMPLES

The following synthetic and biological examples are offered to illustrate this the present technology and are not to be construed in any way as limiting the scope of this the present technology. Unless otherwise stated, all temperatures are in degrees Celsius.

The examples are offered for illustrative purposes only, and are not intended to limit the scope of the present invention in any way. Efforts have been made to ensure accuracy with respect to numbers used (e.g., amounts, temperatures, etc.), but some experimental error and deviation should be allowed for.

The present technology is further understood by reference to the following examples, which are intended to be purely exemplary of the present technology. The present technology is not limited in scope by the exemplified embodiments, which are intended as illustrations of single embodiments of the present technology only. Any methods that are functionally equivalent are within the scope of the present technology. Various modifications of the present technology in addition to those described herein will become apparent to those skilled in the art from the foregoing description and accompanying figures. Such modifications fall within the scope of the appended claims.

In the examples below, the following abbreviations have the following meanings.

If an abbreviation is not defined, it has its generally accepted meaning.

aq.=aqueous
LC-MS=liquid chromatography-mass spectrometry
MS=mass spectrometry
THE=tetrahydrofuran
$NaHCO_3$=sodium bicarbonate
DIEA=diisopropylethylamine
MS=mass spectrometry
NaH=sodium hydride
o/n=overnight
HATU=1-[Bis(dimethylamino)methylene]-1H-1,2,3-trizolo[4,5-b]pyridinium 3-oxid hexafluorophosphate
r.t.=room temperature
LAH=lithium aluminum hydride
DCM=dichloromethane
DMF=dimethylformamide
DMSO=dimethyl sulfoxide
equiv.=equivalent
EtOAc=ethyl acetate
EtOH=ethanol
g=gram
h=hours
HCl=hydrochloric acid
HPLC=high-performance liquid chromatography
HOAc=acetic acid
M=molar
MeOH=methanol
mg=milligrams
mL=milliliters
mmol=millimols
mp=melting point
m/z=mass to charge ratio
NaCl=sodium chloride
$Na_2CO_3$=sodium carbonate
NMR=nuclear magnetic resonance
NaOH=sodium hydroxide
$Na_2SO_4$=sodium sulfate
ppm=parts per million
TFA=trifluoroacetic acid
TLC=thin layer chromatography
TsOH=p-Toluenesulfonic acid
UV=ultraviolet
wt %=weight percent
M=micromolar Example 1—Total Synthesis of SRA737

General Experimental Details:

Final compounds were confirmed by HPLC/MS analysis and determined to be ≥90% pure by weight. $^1H$ and $^{13}C$ NMR spectra were recorded in $CDCl_3$ (residual internal standard $CHCl_3$=δ 7.26), DMSO-$d_6$ (residual internal standard $CD_3SOCD_2H$=δ 2.50), methanol-$d_4$ (residual internal standard $CD_2HOD$=δ 3.20), or acetone-$d_6$ (residual internal standard $CD_3COCD_2H$=δ 2.05). The chemical shifts (δ) reported are given in parts per million (ppm) and the coupling constants (J) are in Hertz (Hz). The spin multiplicities are reported as s=singlet, bs=broad singlet, bm=broad multiplet, d=doublet, t=triplet, q=quartet, p=pentuplet, dd=doublet of doublet, ddd=doublet of doublet of doublet, dt=doublet of triplet, td=triplet of doublet, tt=triplet of triplet, and m=multiplet.

HPLC-MS analysis was carried out with gradient elution. Medium pressure liquid chromatography (MPLC) was performed with silica gel columns in both the normal phase and reverse phase.

Step 1—Synthesis of tert-butyl (R)-2-(((methylsulfonyl)oxy)methyl)morpholine-4-carboxylate

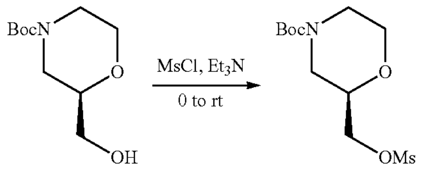

II

Tert-butyl (R)-2-(hydroxymethyl)morpholine-4-carboxylate (1000 g, 4.6 mol, 1.0 eq.) was suspended in MTBE (8600 g, 8.6 w/w) and $Et_3N$ (559 g, 5.52 mol, 1.2 eq.) was added with stirring under a $N_2$ atmosphere. The mixture was cooled to −5° C. and methanesulfonyl chloride (580 g, 5.06 mol, 1.1 eq.) was added dropwise over a period of 15 minutes. The mixture was stirred at 0° C. for 30 minutes then allowed to warm to room temperature over 2 hours. A 10% aq. HCl solution was added (1000 g) and allowed to stir for 10 min at 15° C. The layers were separated and the organic layer was washed with a saturated sodium bicarbonate solution followed by brine. The organic layer was then distilled at atmospheric pressure to reduce the water content and more MTBE was added followed by heptanes. The turbid mixture was seeded with mesylate product seeds and more heptanes were added over 6 hours. The resulting slurry was filtered and washed with heptanes and dried in a vacuum oven to afford the compound of formula II, tert-butyl (R)-2-(((methylsulfonyl)oxy)methyl)morpholine-4-carboxylate as a white crystalline solid (1250 g, with 99.6% purity by weight). $^1H$ NMR (400 MHz, $CDCl_3$) δ (ppm) 4.23 (d, 2H), 3.92 (m, 3H), 3.69 (m, 1H), 3.54 (dt, 1H), 3.07 (s, 3H), 2.95 (br s, 1H), 2.77 (br s, 1H), 1.47 (s, 9H). $^{13}C$ NMR (100 MHz, $CDCl_3$) δ 154.6, 80.5, 73.0, 69.4, 66.5, 37.7, 28.4; HRMS calcd. For $C_{11}H_{22}NO_6S$ [M+H$^+$]: 296.1168; found: 296.1161 DSC 63.92° C. (peak); Pos. [°2Th.] (Rel. Int %) 12.868820 (8.85), 18.084000 (100), 20.606050 (45.58), 21.569860 (21.94), 22.349710 (9.99), 26.472810 (13.55), 27.782060 (10.77).

Step 2—Synthesis of tert-butyl (S)-2-(((2-chloro-5-(trifluoromethyl)pyridin-4-yl)amino)methyl)morpholine-4-carboxylate

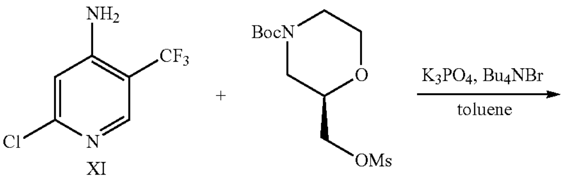

XI II

-continued

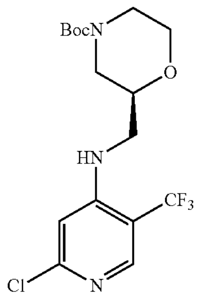

XII

Tert-butyl (R)-2-(((methylsulfonyl)oxy)methyl)morpholine-4-carboxylate (12.8 Kg), 2-chloro-5-(trifluoromethyl) pyridin-4-amine (8.5 Kg, 1.0 eq.), potassium phosphate (36.8 Kg) and tetrabutylammonium bromide (700 g) were suspended in toluene (96 L) and water (400 g) was added. The mixture was heated to 103-108° C. over 2 hours with stirring. After 31 hours the reaction was determined to be complete by HPLC analysis. The mixture was cooled to 0-5° C. and water (77 L) was added over 30 minutes. The aqueous layer was discarded and the organic layer was washed with dilute HCl, a 10% bicarbonate solution and water. The batch was concentrated to approximately 3 volumes and seeded at 35-40° C. and held for 1 hour. The resulting suspension was cooled to 20-25° C. and stirred for 12 hours. The product was collected by filtration, washing with a 3:1 mixture of heptanes and toluene, followed by heptanes. The filter cake was dried to afford the compound of formula XII tert-butyl (S)-2-(((2-chloro-5-(trifluoromethyl)pyridin-4-yl)amino) methyl)morpholine-4-carboxylate as a yellow crystalline solid $^{1}$H NMR (400 MHz, $CDCl_3$) δ (ppm) 8.23 (s, 1H), 6.60 (s, 1H), 5.32 (br s, 1H), 3.93 (br d, 2H), 3.67 (m, 1H), 3.57 (dt, 1H), 3.33 (m, 1H), 3.20 (m, 1H), 2.97 (br m, 4H), 2.76 (br m, 4H), 3.21 (d, 1H), 1.47 (s, 9H), $^{13}$C NMR (100 MHz, $CDCl_3$) δ 156.15, 154.74, 152.27, 147.39 (q, J=6 Hz). 124.44 (q, J=271 Hz) 109.89 (q, J=30 Hz), 105.61, 80.70, 73.03, 66.74, 44.99, 28.54: DSC 108.82° C. (peak); [° 2Th.] (Rel. Int %) 8.0498 (21), 10.6105 (13.86), 12.9914 (25.34), 13.0971 (24.75), 14.7335 (11.00), 16.0964 (71.38), 16.4040 (11.84), 17.0986 (12.15), 17.2313 (18.69), 18.5062 (12.10), 19.0810 (17.33), 19.3499 (100), 20.51.35 (27.49), 20.9726 (20.31), 21.1684 (18.05), 22.9569 (12.14), 23.6437 (29.38), 25.7977 (12.15).

Step 3—Synthesis of tert-butyl (S)-2-(((2-((5-cyanopyrazin-2-yl)amino)-5-(trifluoromethyl)pyridin-4-yl)amino)methyl)morpholine-4-carboxylate

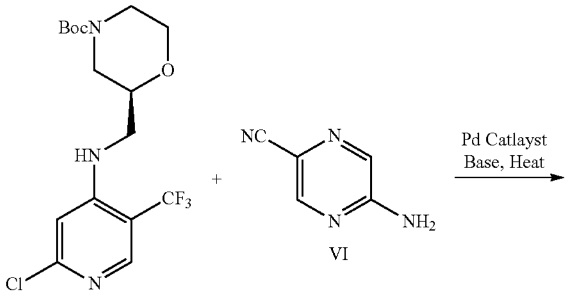

VI

XII

-continued

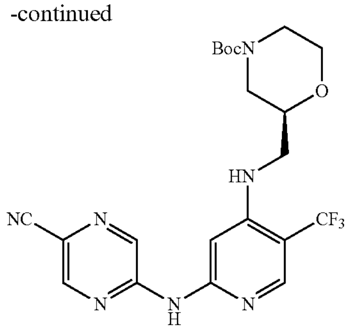

X

To Reactor A was charged tert-butyl (S)-2-(((2-chloro-5-(trifluoromethyl)pyridin-4-yl)amino)methyl)morpholine-4-carboxylate (5.55 Kg), 5-aminopyrazine-2-carbonitrile (1.78 Kg), Palladium Acetate (9.44 g, 0.28 mol %), (R)-1-[(Dicyclohexylphosphino)ferrocenyl]ethyldi-tert-butlyphosphine (23.44 g, 0.30 mol %) followed by 3 cycles of sparging with argon. Degassed DMF (12.9 Kg) was added followed by degassed water (2.22 g) and the solution was stirred for 1 hour under a steady stream of argon. To Reactor B containing degassed DMF (20 L) was added potassium phosphate (3.72 Kg) under a constant argon stream. The slurry was stirred and heated to 125-135° C. The content of Reactor A was added to Reactor B over 45 minutes, keeping the temperature in Reactor B between 125-135° C. The reaction mixture was held at this temperature for 1 hour and HPLC analysis determined the reaction was complete. The mixture was cooled to room temperature and water (8.5 L) was added with stirring, keeping the temperature below 40° C. (at this point the mixture may be seeded). Water (51.2 L) was then added and the slurry was allowed to stir for an additional 30 minutes. The product compound salt of formula IX, tert-butyl (S)-2-(((2-((5-cyanopyrazin-2-yl) amino)-5-(trifluoromethyl)pyridin-4-yl)amino)methyl)morpholine-4-carboxylate, was collected via filtration, washing with 1:1 DMF/water followed by water then heptane and then dried in a vacuum oven to afford the product as a crystalline DMF solvate (7.36 Kg). The DMF solvate product was recrystallized from 3.1 volumes of acetonitrile to afford the non-solvated product as a crystalline solid (79% recovery). $^{1}$H NMR (400 MHz, DMSO) δ (ppm) 10.76 (br s, 1H), 9.05 (d, 1H), 8.78 (d, 1H), 8.21 (s, 1H), 7.28 (s, 1H), 6.51 (br s, 1H), 3.89 (br s, 1H). 3.78 (br dd, 2H), 3.64 (br m, 1H), 3.44-3.27 (br, m, 4H), 2.90 (br s, 1H), 2.66 (br s, 1H), 2.51 (m, 1H), 1.38 (s, 9H). $^{13}$C NMR (100 MHz, DMSO) δ 155.74, 153.88, 151.89, 151.50, 147.19, 145.97 (q, J=7 Hz), 136.83. 124.79 (q, J=269 Hz), 118.78, 117.06, 104.44 (q, J=30 Hz), 93.39, 79.16, 72.58, 65.81, 27.93; DSC 198.37° C. (peak); [° 2Th.] (Rel. Int %) 5.6080 (100), 11.1507 (28.25), 14.8083 (1.74), 16.7334 (9.81), 19.0723 (1.77), 19.4601 (3.46), 24.4798 (0.81), 28.0267 (1.14).

Step 4—Synthesis of (R)-5-((4-((morpholin-2-ylmethyl)amino)-5-(trifluoromethyl)pyridin-2-yl)amino) pyrazine-2-carbonitrile

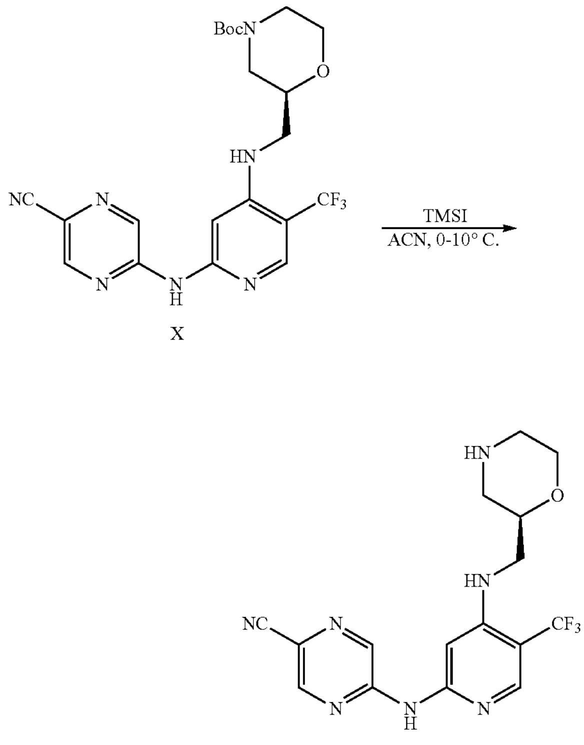

X

VIII

Tert-butyl (S)-2-(((2-((5-cyanopyrazin-2-yl)amino)-5-(trifluoromethyl)pyridin-4-yl)amino)methyl)morpholine-4-carboxylate (6.835 Kg) was added to a reactor followed by acetonitrile (39.98 Kg) and the slurry was cooled to 0-10° C. Iodotrimethylsilane (3.68 Kg) was added over 30 minutes and the clear mixture was allowed to stir for an additional 45 minutes. The reaction mixture was quenched into a 10% potassium carbonate solution (4.1 Kg potassium carbonate) and ethyl acetate was added (36.2 Kg). The resulting slurry was filtered and washed with ethyl acetate (16.5 Kg), water (49.8 Kg) and ethyl acetate (18.4 Kg). The product compound of formula VIII was dried in a vacuum oven to afford (R)-5-((4-((morpholin-2-ylmethyl)amino)-5-(trifluoromethyl)pyridin-2-yl)amino)pyrazine-2-carbonitrile as a crystalline solid (3.88 Kg) with 71.7% isolated yield. $^{1}H$ NMR (400 MHz, DMSO-$d_6$) δ (ppm) 10.76 (br s, 1H), 10.33 (br s, 4H), 9.06 (d, 1H), 8.81 (d, 1H), 8.23 (s, 3H), 7.28 (s, 1H), 6.56 (br t, 1H), 4.00 (dd, 1H), 3.95-3.85 (m, 1H), 3.68 (br t, 1H), 3.40-3.29 (m, 2H), 3.21 (d, 1H), 3.14 (d, 1H), 2.98 (dt, 1H), 2.80 (br t, 1H), 2.58 (d, 2H), 2.51 (2, 2H). $^{13}C$ NMR (100 MHz, DMSO-$d_6$) δ 156.03, 152.07, 151.58, 147.27, 145.91 (q, J=6 Hz), 136.93, 124.89 (q, J=270 Hz), 118.55, 117.22, 104.31 (q, J=29 Hz), 93.40, 73.66, 67.29, 48.94, 45.46, 44.96; DSC 91.25, 227.89° C. (peak); [° 2Th.] (Rel. Int %) 7.8452 (35.54), 10.55754 (98.75), 12.1764 (42.38), 16.09.4 (12.66), 16.8197 (100), 17.0873 (33.00), 17.7144 (9.67), 18.0371 (44.39), 20.5020 (11.45), 21.0506 (14.23), 21.9434 (49.47), 24.3626 (18.77), 25.2738 (34.48), 26.1521 (13.61), 27.0430 (15.52), 32.3872 (21.35), 36.0001 (13.30).

Step 5—Synthesis of (R)-2-(((2-((5-cyanopyrazin-2-yl)amino)-5-(trifluoromethyl)pyridin-4-yl)amino) methyl)morpholin-4-ium 3-carboxy-2-(carboxymethyl)-2-hydroxypropanoate

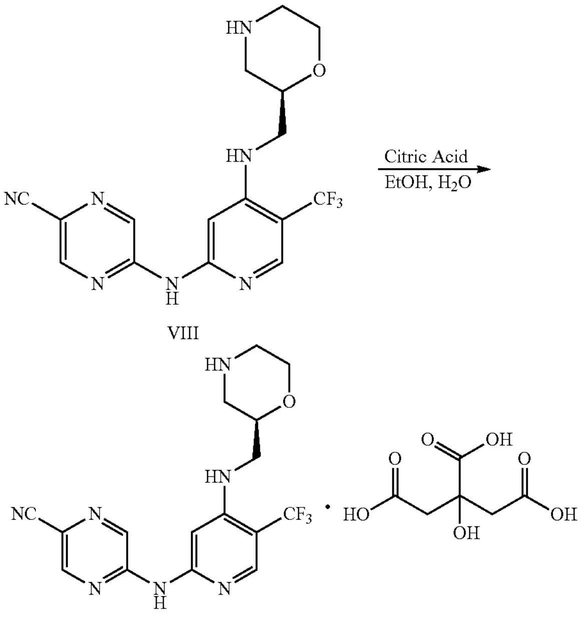

VIII

IX

To a reactor is charged the free base (R)-5-((4-((morpholin-2-ylmethyl)amino)-5-(trifluoromethyl)pyridin-2-yl) amino)pyrazine-2-carbonitrile (7.73 kg), ethanol (36.6 Kg) and water (38.8 Kg). The slurry is briefly heated to 40° C. and cooled to room temperature. Acetic acid is added (2.44 Kg) and the mixture is warmed to 30-35° C. with stirring until a homogeneous mixture is obtained. The warm solution is filtered into another reactor and citric acid is added (786 g in 1 L water) followed by seeds. Citric acid in water (3.9 Kg in 5 L) is added and the slurry is allowed to stir at ambient temperature overnight. The product is isolated via filtration, washing with a 1:1 solution of ethanol and water (2 times) followed by absolute ethanol. The material is dried in a vacuum oven to afford the compound salt of formula IX as a crystalline solid (10.5 Kg). The compound citrate salt is determined to be a 1:1 salt using $^{1}H$ NMR or ion chromatography. $^{1}H$ NMR (400 MHz, DMSO) δ (ppm) 10.76 (br s, 1H), 10.26 (br s, 4H), 9.07 (s, 1H), 8.80 (s, 1H), 8.23 (s, 1H), 7.28 (s, 1H), 6.55 (t, J=8 Hz, 1H), 3.98 (dd, J=12, 4 Hz, 1H), 3.91 (dtd, J=8.1, 5.8, 2.1 Hz, 1H), 3.68 (dt, J=12, 4 Hz 1H), 3.35 (dt, J=8, 4 Hz, 2H), 3.21 (d, J=12 Hz 1H), 3.14 (d, J=12 Hz 1H), 2.98 (dt, J=12, 4 Hz 1H), 2.80 (br t, 1H), 2.56 (ap q, J=16, 4H) Hz. $^{13}C$ NMR (100 MHz, DMSO) δ 176.93, 171.43, 155.79, 151.87, 151.53, 147.32, 146.08 (q, J=6 Hz), 136.80, 124.76 (q, J=270 Hz), 118.86, 117.12, 104.53 (q, J=29 Hz), 93.41, 71.42, 71.14, 63.79, 45.56, 44.40, 44.30, 42.66; FTIR (KBr) $v_{max}$ 3439, 3422, 2996, 2875, 2521, 2229, 1732, 1618, 1578, 1520, 1460, 1441, 1386; [M+H] =380.0; ES Pos.; DSC 206.26° C. (peak); [°2Th.] (Rel. Int %) 5.9735 (100), 14.5577 (14.06), 17.8673 (17.00), 18.8133 (30.79), 23.8752 (17.46), 27.7527 (11.68).

Example 2—Deprotection of the Compound of Formula X on Small and Large Scales with Trifluoroacetic Acid

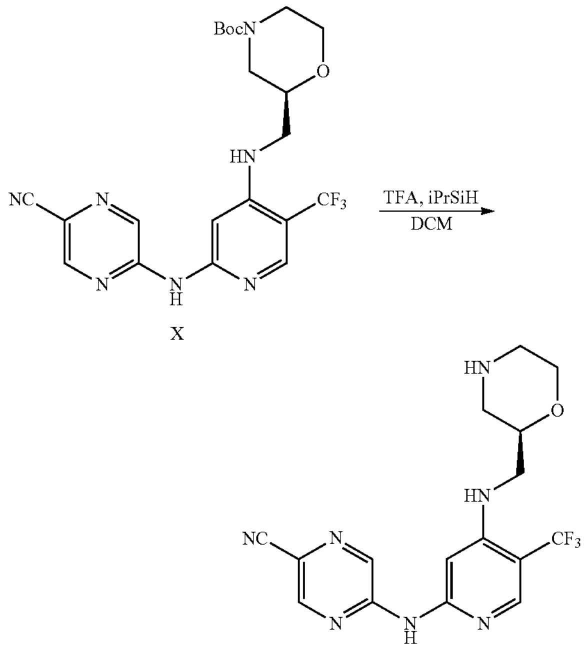

X

VIII

This example shows the differences in reaction profile of the deprotection of the compound of formula X on 1-gram and 10-gram scales to give the free base of SRA737 (formula VIII).

Initially, 1 gram of the compound of formula X was dissolved in DCM followed by the addition of trifluoroacetic acid (TFA) and triisopropylsilane. The profile of the reaction was monitored by LC analysis, which showed that the reaction was completed after 30 minutes. The reaction mixture was then concentrated in vacuo and the resulting crude material was subjected to a DCM and toluene strip out. The crude material was then dissolved in a mixture of DCM and methanol and passed through a 10 g Biotage NH2 isolute cartridge. The product containing fractions were concentrated in vacuo to give a yellow solid. The desired product of formula VIII, as confirmed by 1H NMR analysis, was further analyzed by LC-MS and showed a purity of 94.5%. This crude material was then further purified with 10% methanol in diethyl ether to give the desired product of formula VIII with a purity of >97% in 80% yield.

This deprotection reaction was next repeated on a 10-gram scale. Similar to the 1-gram scale trial, the reaction was completed after 30 minutes. A portion of the reaction mixture was taken out and kept at room temperature overnight to examine the stability of the product in the reaction media, while the remaining mixture was concentrated in vacuo and azeotroped with toluene to give an orange oil. However, LC-MS analysis of this material showed significant degradation with a purity of 77% and two major impurities of 13% and 5% respectively. Examination of the reaction mixture that was kept overnight at room temperature showed degradation to 87% with the same impurities of 9% and 2% respectively.

The impurities formed in this 10-gram scale reaction were identified as the t-butyl amide compound of formula XIII and the corresponding t-butyl methyl imidate compound of formula XIV. Further inspection of the 1-gram reaction also showed the compound of formula XIII as an impurity but in a much lower quantity of <1%, which was easily removed by treatment with 10% methanol in diethyl ether.

XIII

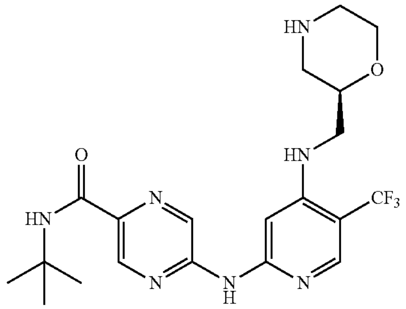

XIV

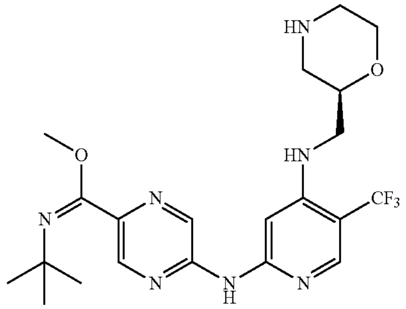

Thus, this example demonstrated that the TFA/DCM deprotection condition was not applicable to large scale manufacturing of the free base of SRA737 from the compound of formula X.

While some embodiments have been illustrated and described, a person with ordinary skill in the art, after reading the foregoing specification, can effect changes, substitutions of equivalents and other types of alterations to the compounds of the present technology or salts, pharmaceutical compositions, derivatives, prodrugs, metabolites, tautomers or racemic mixtures thereof as set forth herein. Each aspect and embodiment described above can also have included or incorporated therewith such variations or embodiments as disclosed in regard to any or all of the other embodiments and embodiments.

The present technology is also not to be limited in terms of the particular embodiments described herein, which are intended as single illustrations of individual embodiments of the present technology. Many modifications and variations of this present technology can be made without departing from its spirit and scope, as will be apparent to those skilled in the art. Functionally equivalent methods within the scope of the present technology, in addition to those enumerated herein, will be apparent to those skilled in the art from the foregoing descriptions. Such modifications and variations are intended to fall within the scope of the appended claims. It is to be understood that this present technology is not limited to particular methods, reagents, compounds, compositions, labeled compounds or biological systems, which can, of course, vary. It is also to be understood that the terminology used herein is for the purpose of describing particular embodiments only, and is not intended to be limiting. Thus, it is intended that the specification be considered as exemplary only with the breadth, scope and spirit of the present technology indicated only by the appended claims, definitions therein and any equivalents thereof.

In addition, where features or embodiments of the disclosure are described in terms of Markush groups, those skilled in the art will recognize that the disclosure is also thereby described in terms of any individual member or subgroup of members of the Markush group. Each of the narrower species and subgeneric groupings falling within the generic disclosure also from part of the present technology. This includes the generic description of the present technology with a proviso or negative limitation removing any subject matter from the genus, regardless of whether or not the excised material is specifically recited herein.

All publications, patent applications, issued patents, and other documents (for example, journals, articles and/or textbooks) referred to in this specification are herein incorporated by reference as if each individual publication, patent application, issued patent, or other document was specifically and individually indicated to be incorporated by reference in its entirety. Definitions that are contained in text incorporated by reference are excluded to the extent that they contradict definitions in this disclosure.

Other embodiments are set forth in the following claims, along with the full scope of equivalents to which such claims are entitled.

While the invention has been particularly shown and described with reference to a preferred embodiment and various alternate embodiments, it will be understood by persons skilled in the relevant art that various changes in form and details can be made therein without departing from the spirit and scope of the invention.

All references, issued patents and patent applications cited within the body of the instant specification are hereby incorporated by reference in their entirety, for all purposes.

The invention claimed is:

1. A crystalline form of a compound salt of formula IX:

IX

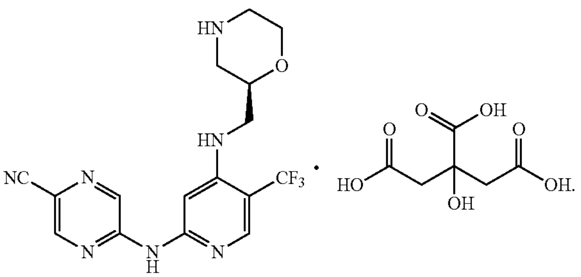

having an X-ray powder diffraction (XRPD) pattern comprising peaks, in terms of 2-theta, at about 5.9°, about 11.8°, about 14.5°, about 18.7°, about 19.3°, about 20.6°, about 20.9°, about 23.0°, and about 24.7°.

2. The crystalline form of claim 1, wherein the crystalline form further comprises peaks, in terms of 2-theta, at about 11.3°, about 14.8°, about 17.8°, about 18.4°, about 19.0°, about 20.2°, about 21.2°, about 21.7°, about 23.7°, about 24.0°, and about 24.4°.

3. The crystalline form of claim 1, wherein the crystalline form has a Differential Scanning calorimetry (DSC) endothermic peak at about 206.26° C.

* * * * *